United States Patent
Jin

(10) Patent No.: US 10,141,523 B2
(45) Date of Patent: Nov. 27, 2018

(54) SOLUTION PROCESSABLE RED-EMITTING IRIDIUM (III) COMPLEX AND ORGANIC ELECTROLUMINESCENCE DEVICE INCLUDING THE SAME

(71) Applicant: LG Chem, Ltd., Seoul (KR)

(72) Inventor: Sung Ho Jin, Busan (KR)

(73) Assignee: LG Chem, Ltd. (KR)

( * ) Notice: Subject to any disclaimer, the term of this patent is extended or adjusted under 35 U.S.C. 154(b) by 517 days.

(21) Appl. No.: 14/648,395

(22) PCT Filed: Nov. 26, 2014

(86) PCT No.: PCT/KR2014/011424
§ 371 (c)(1),
(2) Date: May 29, 2015

(87) PCT Pub. No.: WO2015/129994
PCT Pub. Date: Sep. 3, 2015

(65) Prior Publication Data
US 2016/0308148 A1    Oct. 20, 2016

(30) Foreign Application Priority Data

Feb. 25, 2014  (KR) .................. 10-2014-0021930
Nov. 10, 2014  (KR) .................. 10-2014-0155270

(51) Int. Cl.
| | | |
|---|---|---|
| H01L 51/54 | (2006.01) |
| C09K 11/06 | (2006.01) |
| H01L 51/00 | (2006.01) |
| C07F 15/00 | (2006.01) |
| H01L 51/50 | (2006.01) |

(52) U.S. Cl.
CPC ...... *H01L 51/0085* (2013.01); *C07F 15/0033* (2013.01); *C09K 11/06* (2013.01); *C09K 2211/1007* (2013.01); *C09K 2211/1029* (2013.01); *C09K 2211/1048* (2013.01); *C09K 2211/1092* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 7,560,176 B2 | 7/2009 | Cheng et al. | |
| 9,748,499 B2 * | 8/2017 | Kim et al. | .......... H01L 51/0085 |
| 2006/0237715 A1 * | 10/2006 | Park et al. | .......... C07F 15/0033 |
| | | | 257/40 |
| 2009/0174316 A1 | 7/2009 | Kim et al. | |
| 2014/0367650 A1 | 12/2014 | Kim et al. | |

FOREIGN PATENT DOCUMENTS

| | | |
|---|---|---|
| KR | 10-2005-0014708 A | 2/2005 |
| KR | 10-2008-0044154 A | 5/2008 |
| KR | 10-2009-0045486 A | 5/2009 |
| KR | 10-1065541 B1 | 9/2011 |
| KR | 10-2014-0144998 A | 12/2014 |

OTHER PUBLICATIONS

Giridhar et al., "An electron transporting unit linked multifunctional Ir(III) complex . . . organic light-emitting diodes", Chem. Commun., 2014, 50, pp. 4000-4002 (Feb. 25, 2014).*
English Abstract, KR 20100110959 A (2 pages), 2010.
English Abstract, KR 102008044154A (2 pages), 2008.

* cited by examiner

*Primary Examiner* — Marie R. Yamnitzky
(74) *Attorney, Agent, or Firm* — Lerner, David, Littenberg, Krumholz & Mentlik, LLP

(57) ABSTRACT

The present invention relates to a novel solution processable red-emitting iridium (III) complex. In the iridium (III) complex, a quinoline-thiophene derivative is introduced as a main ligand and a picolinic acid derivative substituted with a halogen, a substituent having electron transporting properties or a substituent having hole transporting properties is introduced as an ancillary ligand at the para-position relative to the nitrogen atom of picolinic acid. The iridium (III) complex is a red phosphorescent compound that is highly electrically stable, exhibits excellent luminescent properties and high luminance, and has high color purity. In addition, the iridium (III) complex has improved solubility in organic solvents and good resistance to heat, ensuring excellent interfacial properties with electrodes. Therefore, the iridium (III) complex is useful as a light emitting material for an organic electroluminescence device. The present invention also relates to an organic electroluminescence device including the iridium (III) complex.

18 Claims, 7 Drawing Sheets

【Figure 1】
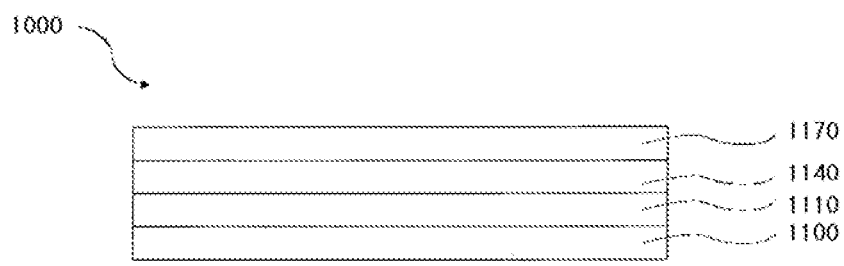
【Figure 2】
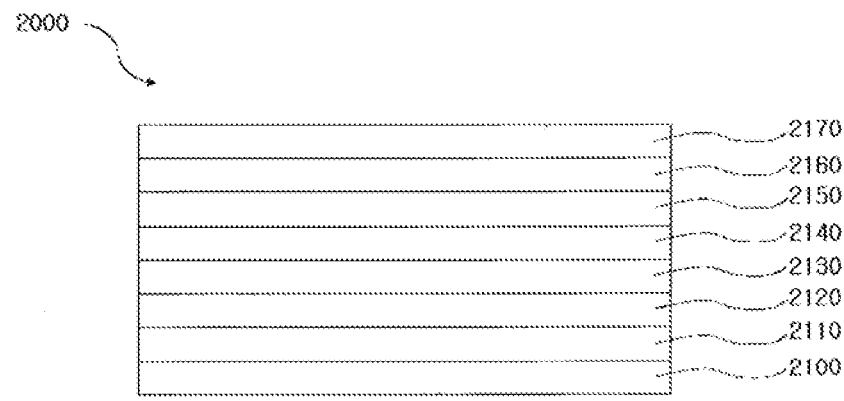

[Figure 3]
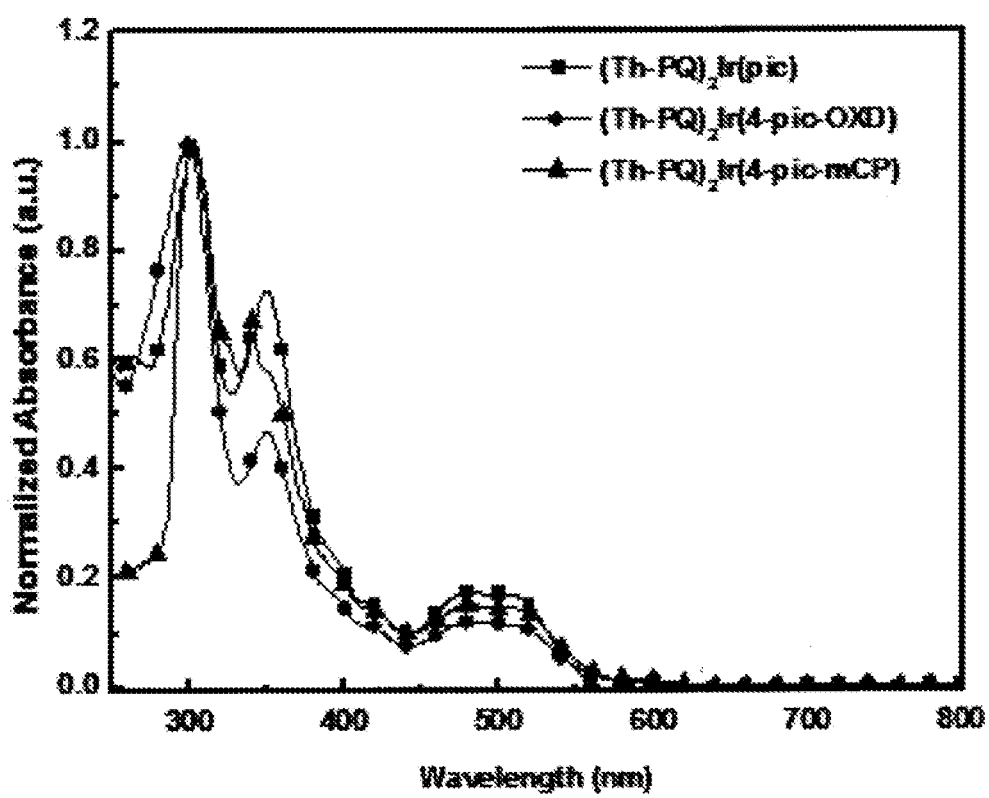

【Figure 4】
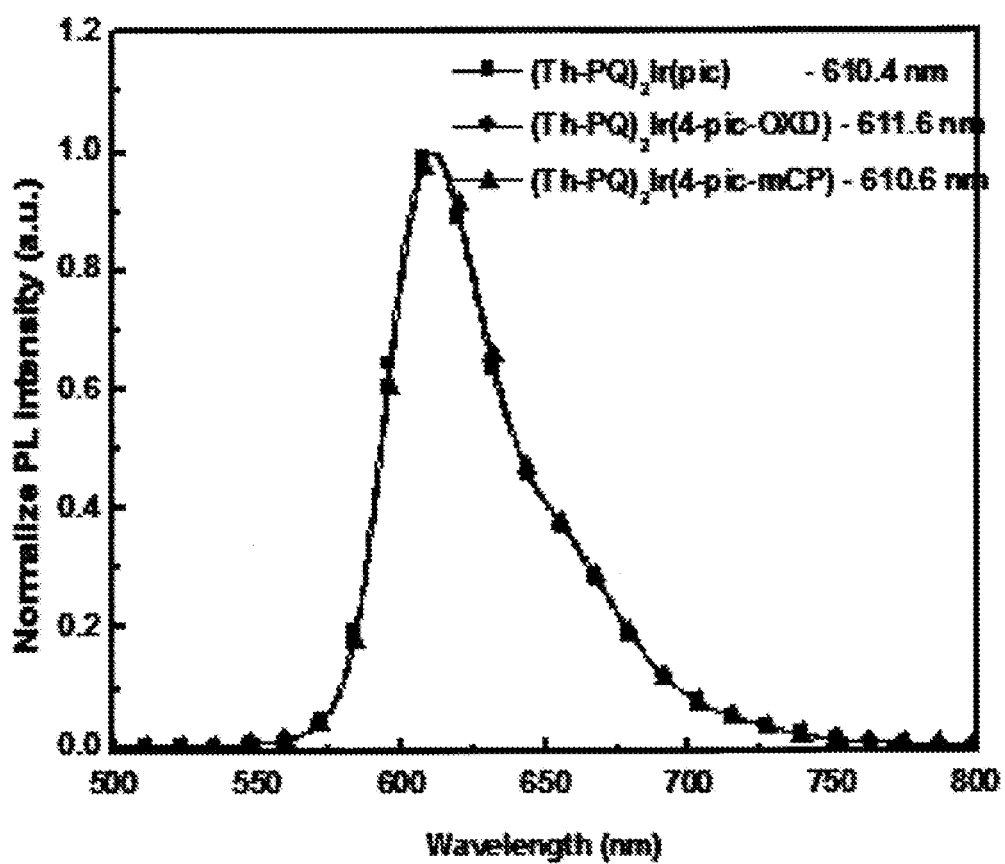

【Figure 5】
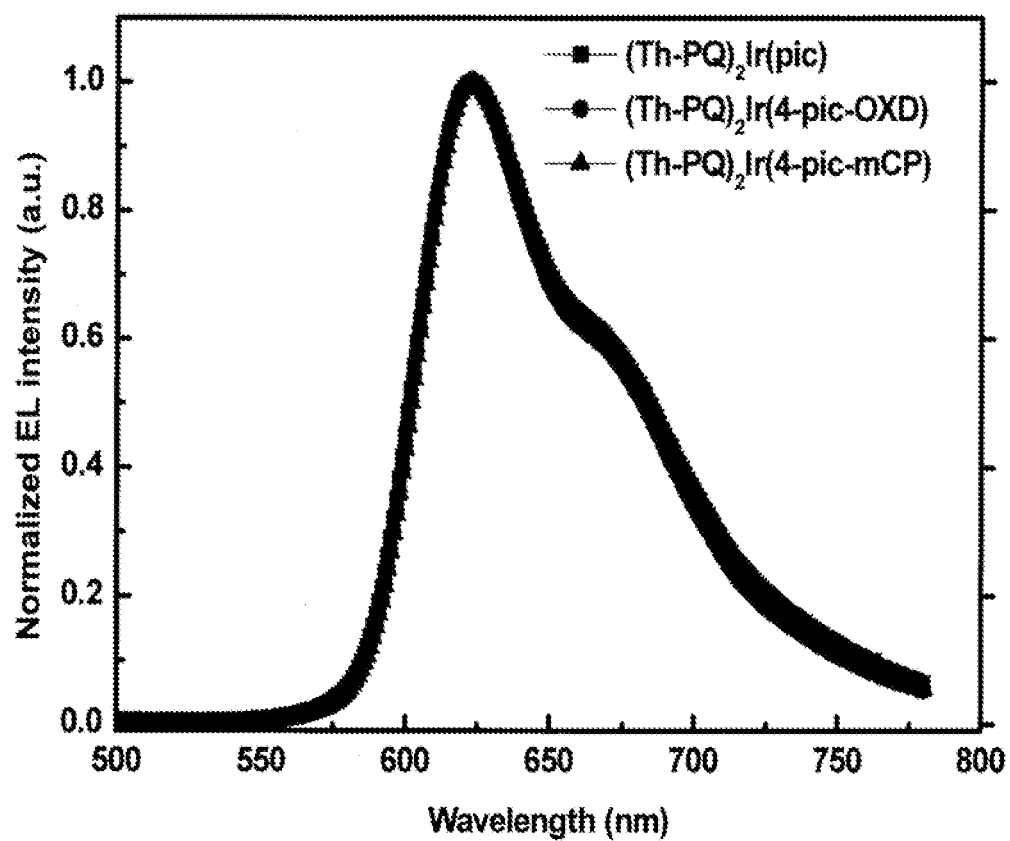

【Figure 6】
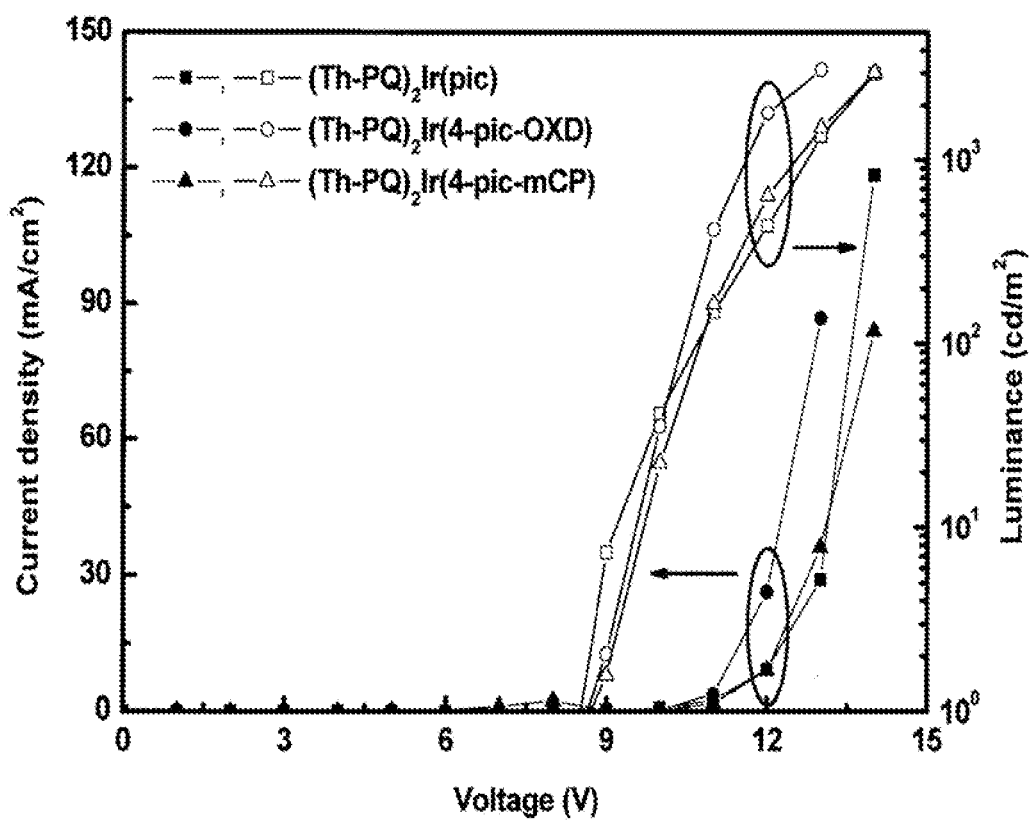

【Figure 7】
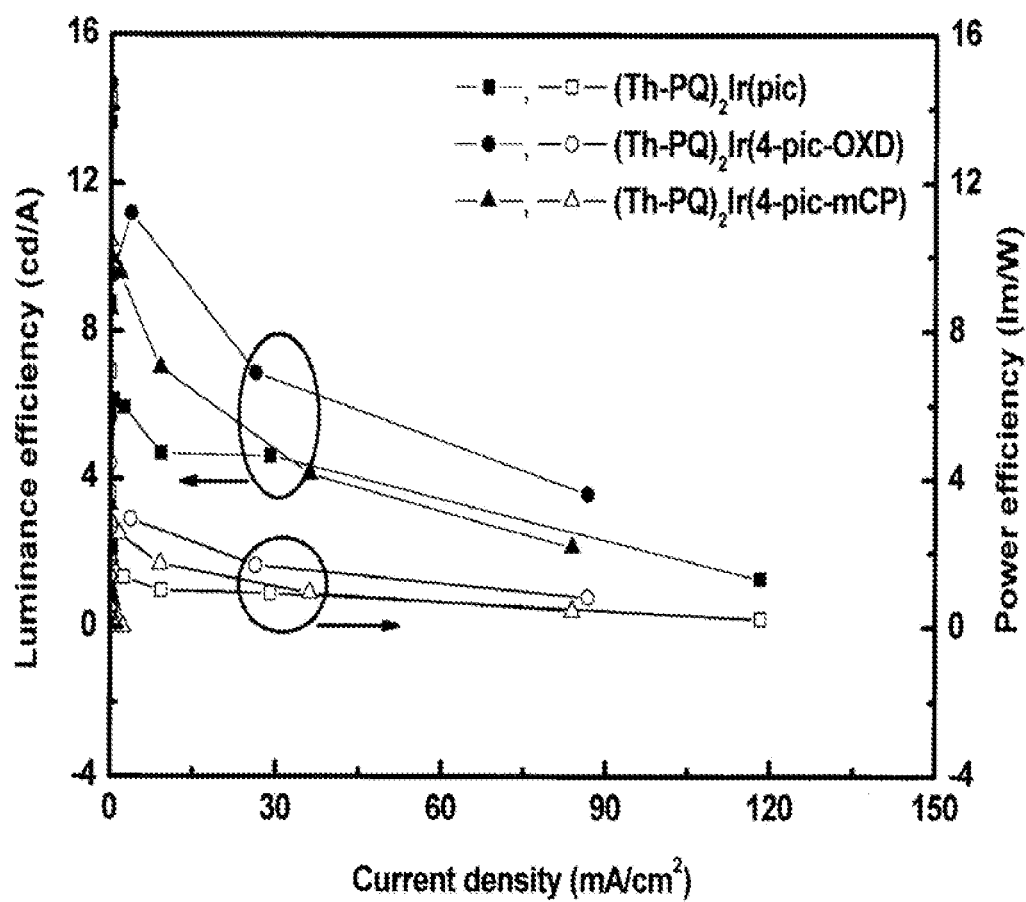

【Figure 8】
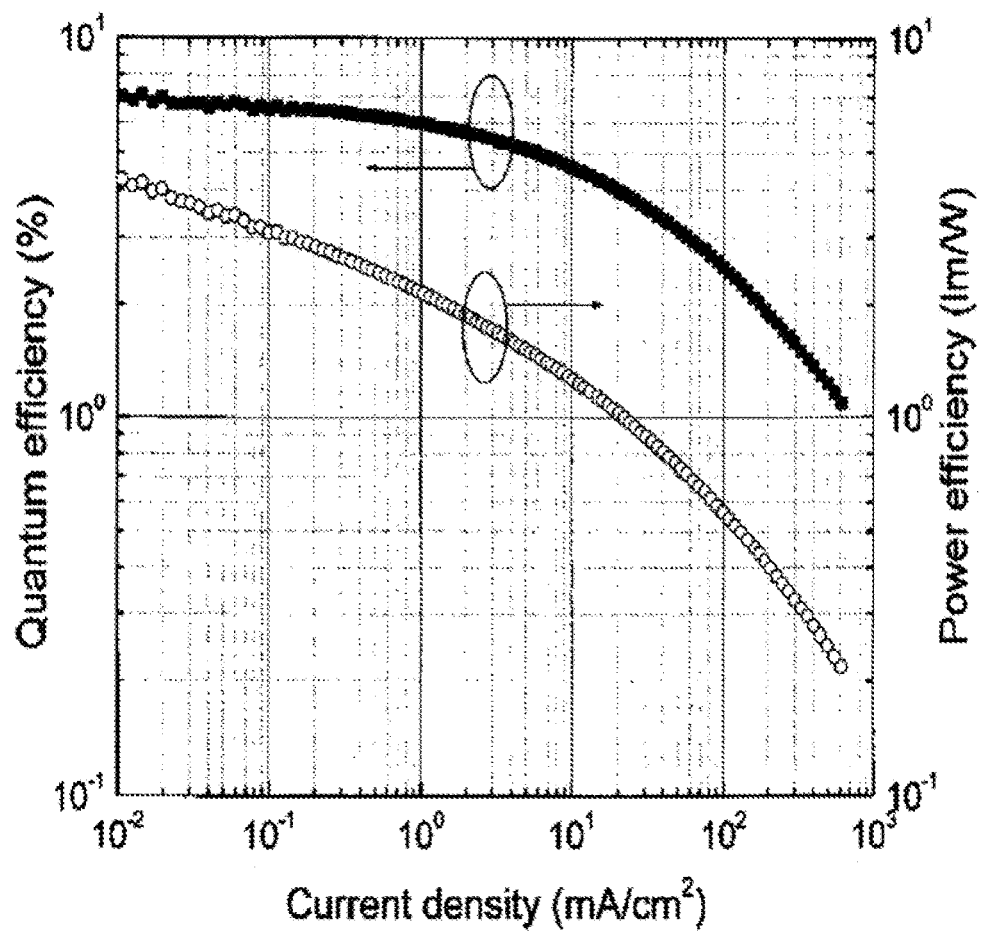

SOLUTION PROCESSABLE RED-EMITTING IRIDIUM (III) COMPLEX AND ORGANIC ELECTROLUMINESCENCE DEVICE INCLUDING THE SAME

TECHNICAL FIELD

The present invention relates to a novel solution processable red-emitting iridium (III) complex and an organic electroluminescence device including the same. More specifically, the present invention relates to a novel iridium (III) complex in which a quinoline-thiophene derivative is introduced as a main ligand and a picolinic acid derivative including a halogen or a substituent having electron transporting or hole transporting properties is introduced as an ancillary ligand at the para-position relative to the nitrogen atom of picolinic acid, and an organic electroluminescence device including the iridium (III) complex.

BACKGROUND

With the recent trend toward large-sized displays, there is an increasing demand for flat panel displays, such as liquid crystal displays (LCDs) and plasma display panels (PDPs). These flat panel displays have slow response time and limited viewing angle compared to CRTs. Under such circumstances, other types of displays, typified by electroluminescence devices, are currently being investigated to replace flat panel displays.

Conventional electroluminescence devices are based on the phenomenon that inorganic semiconductors (for example, ZnS and CaS) having p-n junctions emit light when an electric field is applied thereto. However, the conventional inorganic electroluminescence devices require a driving voltage of at least 220 V AC and are fabricated under vacuum, making it difficult to fabricate in large sizes. Particularly, blue light with high efficiency is difficult to obtain from the conventional inorganic electroluminescence devices.

In attempts to solve such problems, organic electroluminescence devices (for example, organic light-emitting diodes (OLEDs)) using organic materials are being investigated. Organic electroluminescence devices use self-luminous organic materials and are based on the principle of electroluminescence in which when an electric field is applied to an organic material, electrons transported from a cathode and holes transported from an anode recombine in the organic material layer to produce energy, which is emitted as light. In comparison with LCDs, organic electroluminescence devices have the advantages of large viewing angle, low power consumption, and fast response, enabling processing of high-quality images. Due to these advantages, organic electroluminescence devices are attracting attention as next-generation display devices.

The phenomenon of light emission from organic electroluminescence devices can be largely divided into fluorescence and phosphorescence. Fluorescence refers to a phenomenon wherein light emits when an organic molecule decays from the singlet excited state back to the ground state, while phosphorescence refers to a phenomenon wherein light emits when an organic molecule decays from the triplet excited state back to the ground state.

Electrophosphorescence devices were developed by a team led by Professor S. R. Forrest at the Princeton University and Professor M. E. Thompson at the USC in 1999. The electrophosphorescence devices have markedly improved luminance efficiency compared to organic electroluminescence devices. Particularly, since spin-orbit coupling is proportional to the fourth power of atomic number, complexes of heavy atoms, such as platinum (Pt), iridium (Ir), europium (Eu), and terbium (Tb), are known to have high phosphorescence efficiency. The lowest triplet exciton of a platinum complex is a ligand-centered (LC) exciton but that of an iridium complex is a metal-ligand charge transfer (MLCT) exciton. Accordingly, the iridium complex forms stronger spin-orbit coupling and exhibits higher phosphorescence efficiency with much shorter triplet exciton lifetime than the platinum complex.

In this regard, C. Adachi et al. reported an organic electroluminescence device having a maximum luminance efficiency of ~60 lm/w and a maximum internal quantum efficiency of ~87% by doping bis(2-phenylpyridine)iridium (III) acetylacetonate [(ppy)$_2$Ir(acac)], a green phosphorescent dye whose central metal is iridium, into 3-phenyl-4-(1'-naphthyl)-5-phenyl-1,2,4-triazole (TAZ). Further, Universal Display Corp. (UDC, USA) released that a high luminance efficiency of 82 lm/W was achieved by doping the green phosphorescent dye into a light emitting layer and using a hole injecting material developed by LG Chem. (Korea).

Organic electrophosphorescence devices capable of emitting blue, green, and red light were developed, but organic electrophosphorescence devices that can emit three primary colors and are excellent in terms of luminance efficiency, color coordinates, and lifetime, have not been reported, to our knowledge.

In this connection, U.S. Pat. No. 7,250,512 discloses iridium (III) bis(2-(2-benzothienyl)pyridinato-N,C2)(acetylacetonate) [Ir(btp)$_2$(acac)] as a red-emitting iridium complex. However, there is still a need for a novel compound that is satisfactory in terms of color purity, efficiency, and solubility.

SUMMARY

The present invention has been made in an effort to solve the above problems, and it is an object of the present invention to provide a novel red phosphorescent iridium (III) complex in which a quinoline-thiophene derivative is introduced as a main ligand and a picolinic acid derivative including a halogen or a substituent having electron transporting or hole transporting properties is introduced as an ancillary ligand at the para-position relative to the nitrogen atom of picolinic acid.

It is a further object of the present invention to provide an organic electroluminescence device including a light emitting layer including the iridium (III) complex.

One aspect of the present invention provides an iridium (III) complex represented by Formula 1:

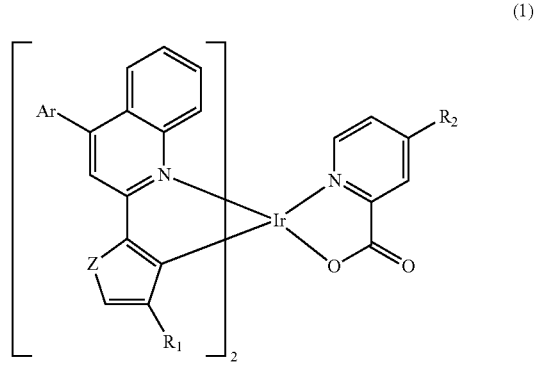

(1)

wherein Ar is C$_6$-C$_{20}$ aryl or C$_3$-C$_{20}$ heteroaryl,
Z is O, S or Se,
R$_1$ is hydrogen, halogen, C$_1$-C$_{20}$ alkyl, C$_1$-C$_{20}$ alkoxy, cyano or nitro,

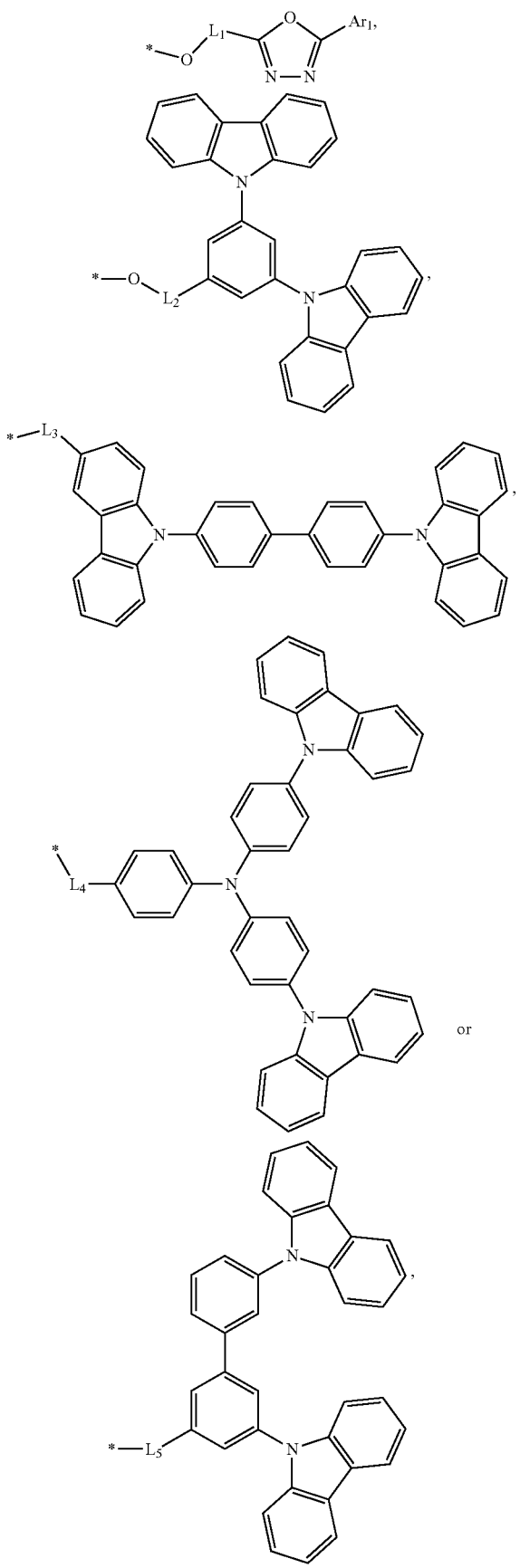

$R_2$ is halogen, $L_1$ is $C_6$-$C_{20}$ arylene, $Ar_1$ is $C_6$-$C_{20}$ aryl, $L_2$ and $L_3$ are each independently $C_1$-$C_{20}$ alkyl, $L_4$ and $L_5$ are each independently O or $C_1$-$C_{20}$ alkoxy, the aryl and heteroaryl of Ar are each independently optionally substituted with one or more substituents selected from halogen, hydroxyl, $C_1$-$C_{10}$ alkyl, $C_1$-$C_{10}$ alkoxy, $C_3$-$C_{20}$ cycloalkyl, and $C_6$-$C_{20}$ aryl, and the heteroaryl of Ar includes one or more heteroatoms selected from N, O, and S.

A further aspect of the present invention provides an organic electroluminescence device including a light emitting layer including the iridium (III) complex represented by Formula 1.

The iridium (III) complex of the present invention is a red phosphorescent compound and has a structure in which a quinoline-thiophene derivative is introduced as a main ligand and a picolinic acid derivative substituted with a halogen, a substituent having electron transporting properties or a substituent having hole transporting properties is introduced as an ancillary ligand at the para-position relative to the nitrogen atom of picolinic acid. Due to this structure, the iridium (III) complex of the present invention not only exhibits excellent luminescent properties and high luminance but also has high color purity. Particularly, the iridium (III) complex of the present invention can exhibit very high external quantum efficiency. In addition, the iridium (III) complex of the present invention has improved solubility in organic solvents and good resistance to heat, ensuring excellent interfacial properties with electrodes. Therefore, the iridium (III) complex of the present invention can be solution processed to fabricate an organic electroluminescence device.

BRIEF DESCRIPTION OF THE DRAWINGS

FIG. 1 is a cross-sectional view schematically illustrating an organic electroluminescence device having a monolayer structure in which an iridium (III) complex of the present invention is applied.

FIG. 2 is a cross-sectional view schematically illustrating an organic electroluminescence device having a multilayer structure in which an iridium (III) complex of the present invention is applied.

FIG. 3 shows UV-visible absorption spectra of iridium (III) complexes synthesized in Examples 2 and 3 and Comparative Example 1.

FIG. 4 is a graph showing the photoluminescence (PL) intensities of iridium (III) complexes synthesized in Examples 2 and 3 and Comparative Example 1.

FIG. 5 is a graph showing the electroluminescence (EL) intensities of organic electroluminescence devices including iridium (III) complexes synthesized in Examples 2 and 3 and Comparative Example 1.

FIG. 6 is a graph showing the current density-voltage-luminance characteristics of organic electroluminescence devices including iridium (III) complexes synthesized in Examples 2 and 3 and Comparative Example 1.

FIG. 7 is a graph showing the external quantum efficiencies of iridium (III) complexes synthesized in Examples 2 and 3 and Comparative Example 1.

FIG. 8 is a graph showing the external quantum efficiencies of an iridium complex according to the prior art.

| * Explanation of reference numerals * ||
|---|---|
| 1000, 2000: Organic electroluminescence devices | 1100, 2100: Substrates |
| 1110, 2110: First electrodes | 2120: Hole injection layer |
| 2130: Hole transporting layer | 1140, 2140: Light emitting layers |
| 2150: Electron transporting layer | 2160: Electron injection layer |
| 1170, 2170: Second electrodes | |

DETAILED DESCRIPTION

The present invention is directed to a novel solution processable red-emitting iridium (III) complex in which a quinoline-thiophene derivative is introduced as a main ligand and a picolinic acid derivative substituted with a halogen or a substituent having electron transporting or hole transporting properties is introduced as an ancillary ligand at the para-position relative to the nitrogen atom of picolinic acid, and an organic electroluminescence device including the iridium (III) complex.

The present invention will now be described in detail.

In one aspect, the present invention provides an iridium (III) complex represented by Formula 1:

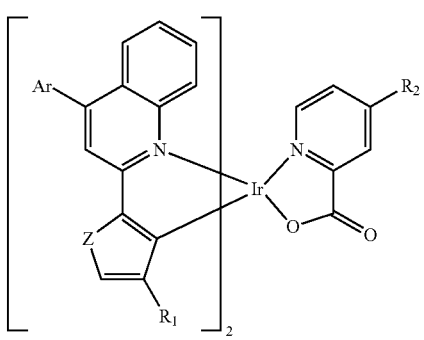

(1)

wherein Ar is $C_6$-$C_{20}$ aryl or $C_3$-$C_{20}$ heteroaryl,

Z is O, S or Se, $R_1$ is hydrogen, halogen, $C_1$-$C_{20}$ alkyl, $C_1$-$C_{20}$ alkoxy, cyano or nitro,

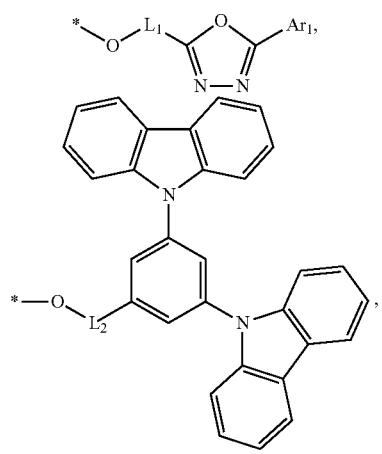

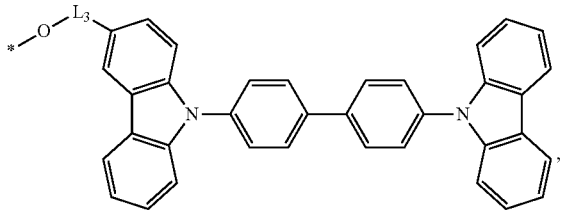

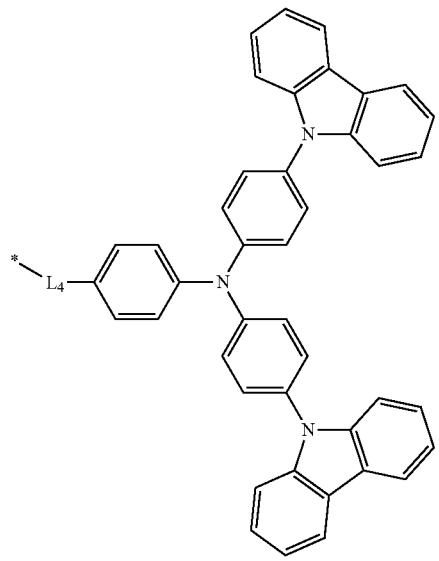

or

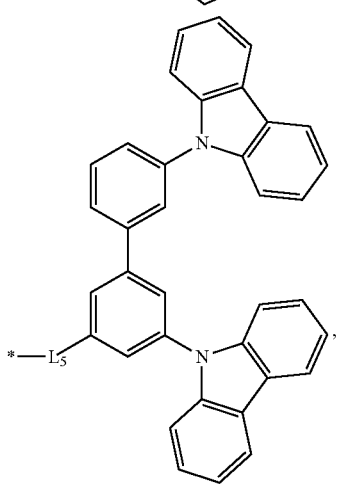

$R_2$ is halogen, $L_1$ is $C_6$-$C_{20}$ arylene, $Ar_1$ is $C_6$-$C_{20}$ aryl, $L_2$ and $L_3$ are each independently $C_1$-$C_{20}$ alkyl, $L_4$ and $L_5$ are each independently O or $C_1$-$C_{20}$ alkoxy, the aryl and heteroaryl of Ar are each independently optionally substituted with one or more substituents selected from halogen, hydroxyl, $C_1$-$C_{10}$ alkyl, $C_1$-$C_{10}$ alkoxy, $C_3$-$C_{20}$ cycloalkyl, and $C_6$-$C_{20}$ aryl, and the heteroaryl of Ar includes one or more heteroatoms selected from N, O, and S.

Preferably, Ar is $C_6$-$C_{20}$ aryl, Z is S, $R_1$ is hydrogen, $R_2$ is halogen,

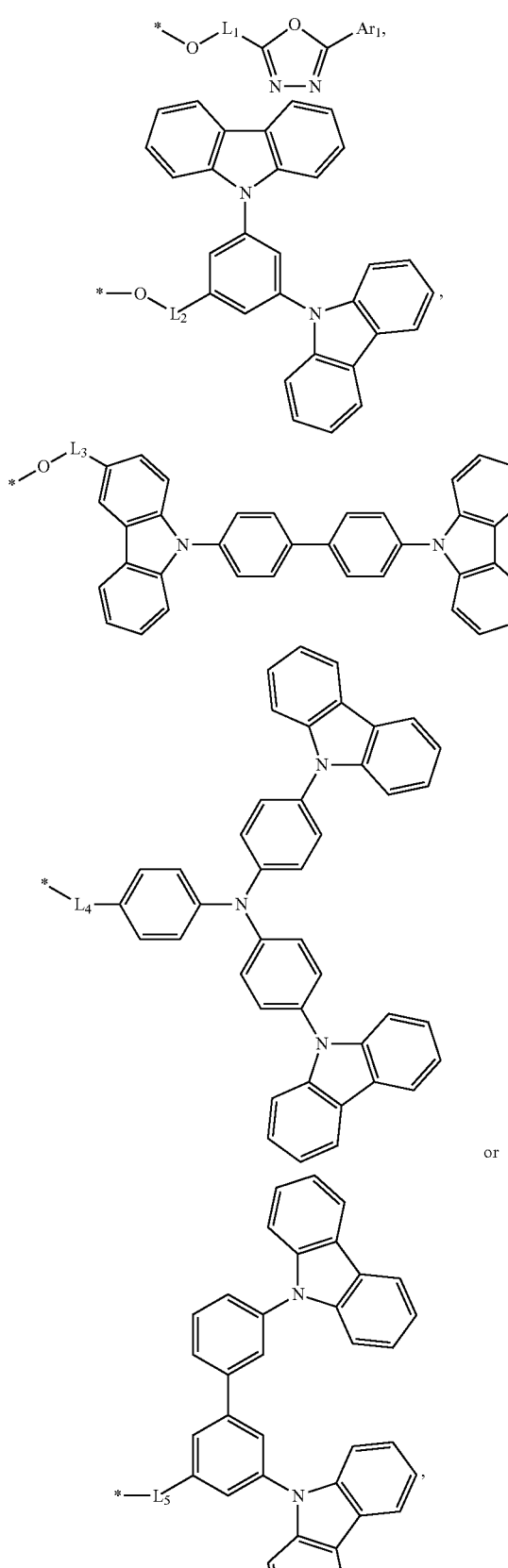
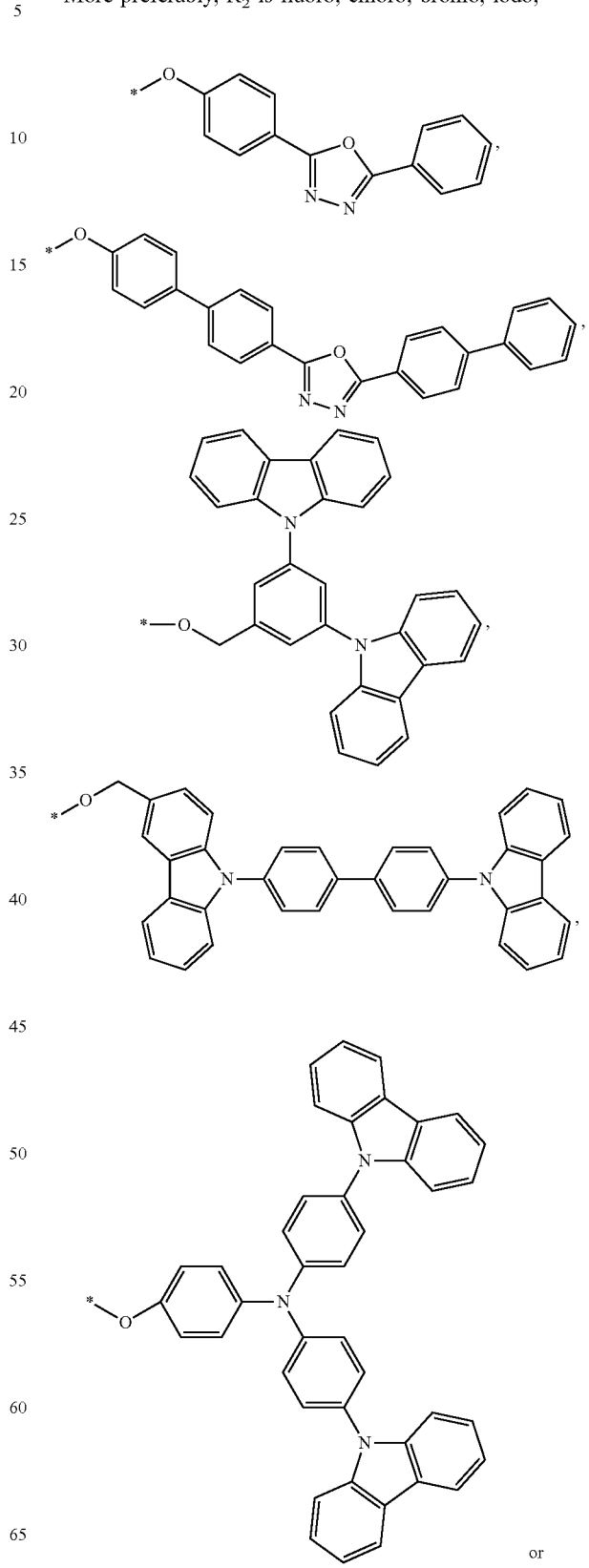
$L_1$ is $C_6$-$C_{20}$ arylene, $Ar_1$ is $C_6$-$C_{20}$ aryl, $L_2$ and $L_3$ are each independently $C_1$-$C_{20}$ alkyl, and $L_4$ and $L_5$ are each independently O or $C_1$-$C_{20}$ alkoxy.
More preferably, $R_2$ is fluoro, chloro, bromo, iodo,

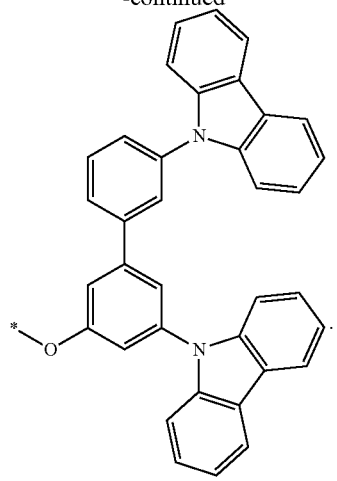
Specifically, the iridium (III) complex represented by Formula 1 may be selected from, but not limited to, the following compounds:
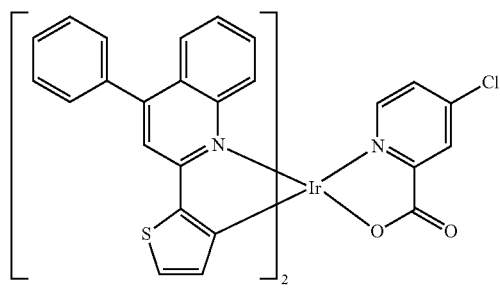
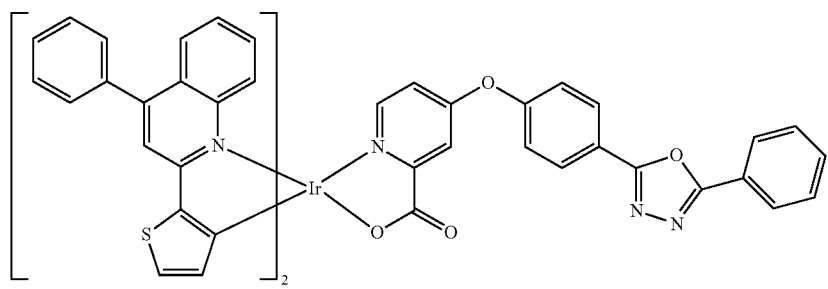
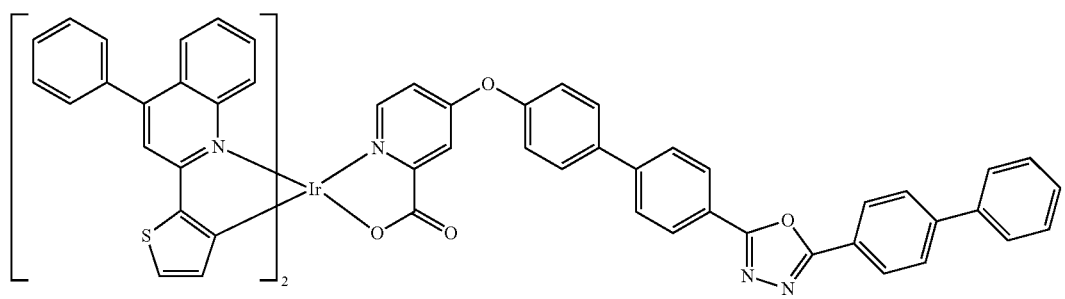

-continued

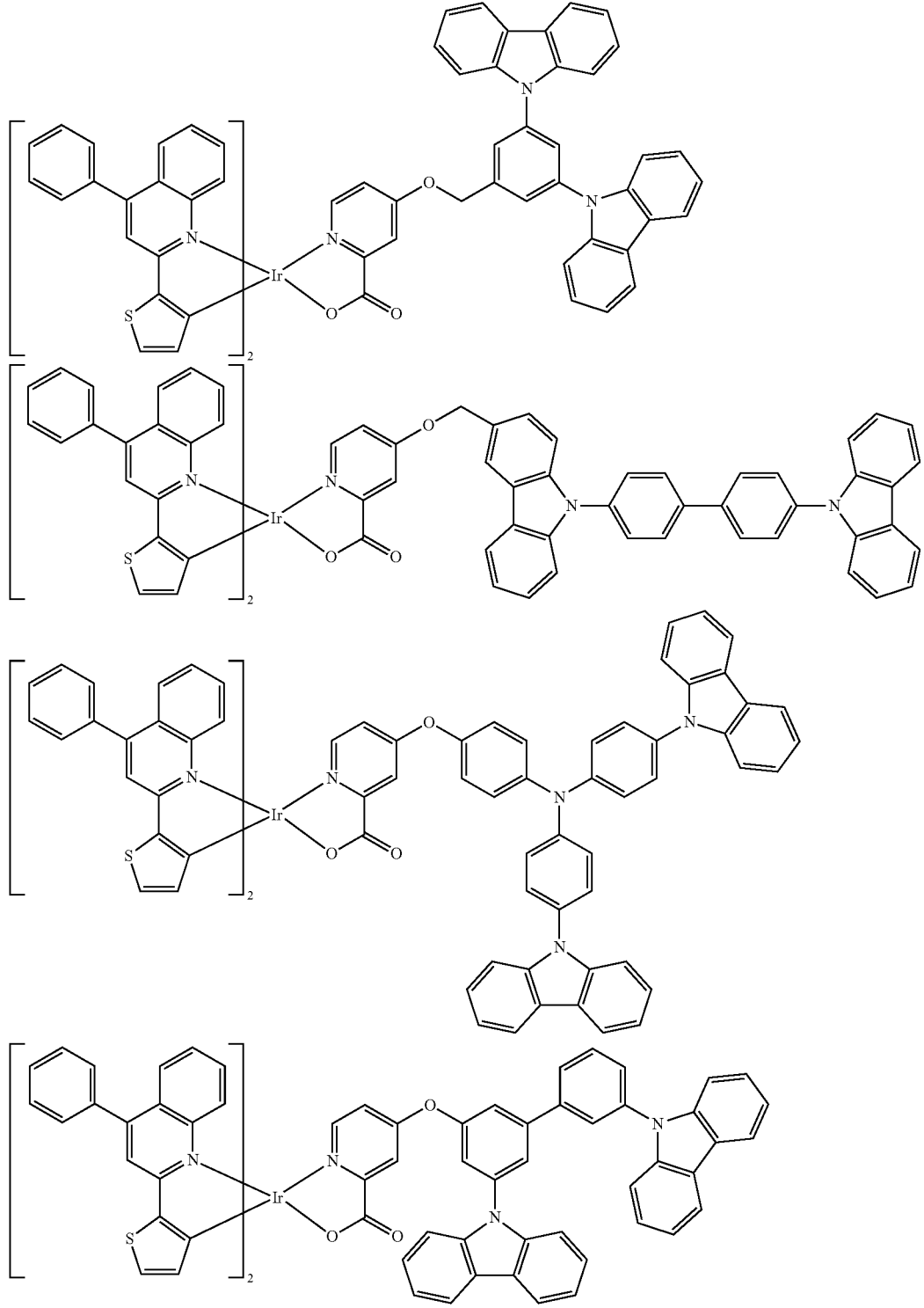

A main ligand of a phosphorescent iridium complex is a major factor determining the emission color of the phosphorescent iridium complex. The iridium (III) complex of the present invention includes a quinoline-thiophene derivative introduced as a main ligand, achieving pure red light emission.

In addition to the main ligand, a picolinic acid derivative is introduced as an ancillary ligand in the iridium (III) complex of the present invention. The ancillary ligand makes the iridium (III) complex readily soluble in organic solvents, enabling solution processing of the iridium (III) complex. Particularly, the picolinic acid derivative is substituted with a halogen, a substituent having electron transporting properties or a substituent having hole transport properties at the para-position relative to the nitrogen atom of picolinic acid. The substituent having electron transporting properties may be an oxadiazole derivative and the substituent having hole transporting properties may be a (3,5-di(9H-carbazol-9-yl)phenyl)methanol (mCP), (9-4(4-(9H-carbazol-9-yl)biphenyl-4-yl)-9H-carbazol-3-yl)methanol (CBP), 3,3-bis(carbazol-9-yl)biphenyl (mCBP) or 4,4-bis(carbazol-9-yl)triphenylamine (BCTA) derivative. This substitution improves the luminescent properties (e.g., emission color), color purity, and luminance efficiency of the iridium (III) complex.

The introduction of the quinoline-thiophene derivative as a main ligand and a picolinic acid derivative substituted with a halogen or a substituent having electron transporting or hole transporting properties as an ancillary ligand at the para-position relative to the nitrogen atom of picolinic acid leads to considerable improvements in the emission color and luminance efficiency of the iridium (III) complex and makes the iridium (III) complex readily soluble in organic solvents. As a result, the iridium (III) complex has improved heat resistance, excellent interfacial properties with electrodes, and outstanding thin film characteristics while maintaining light emission over a large area, thus being suitable for use as a pure red light emitting material.

In a further aspect, the present invention provides a method for synthesizing an iridium (III) complex represented by Formula 1:

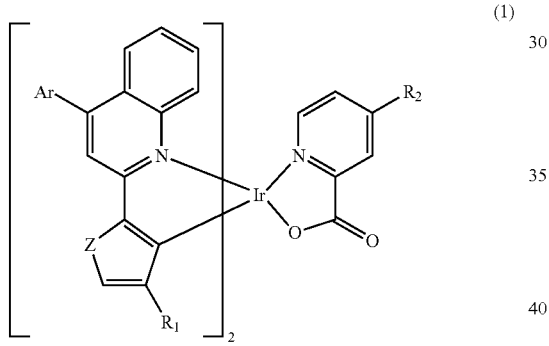

(1)

wherein Ar is $C_6$-$C_{20}$ aryl or $C_3$-$C_{20}$ heteroaryl,

Z is O, S or Se, $R_1$ is hydrogen, halogen, $C_1$-$C_{20}$ alkyl, $C_1$-$C_{20}$ alkoxy, cyano or nitro,

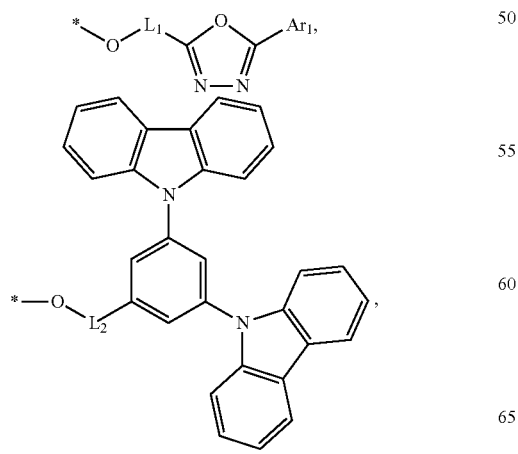

-continued

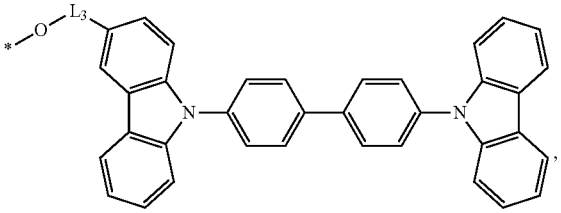

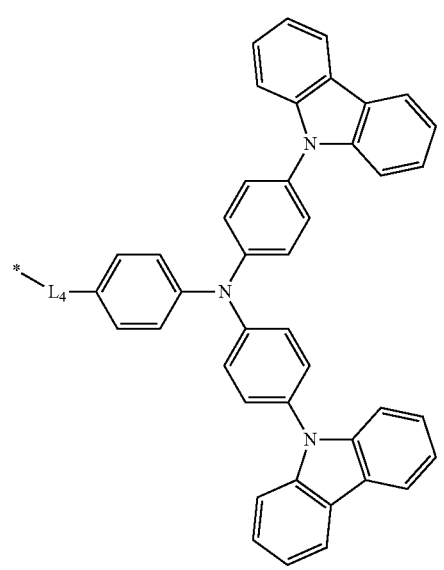

or

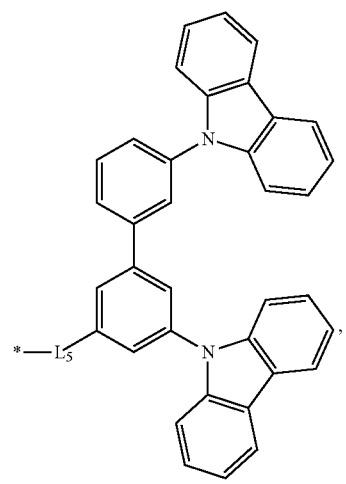

$R_2$ is halogen, $L_1$ is $C_6$-$C_{20}$ arylene, $Ar_1$ is $C_6$-$C_{20}$ aryl, $L_2$ and $L_3$ are each independently $C_1$-$C_{20}$ alkyl, $L_4$ and $L_5$ are each independently O or $C_1$-$C_{20}$ alkoxy, the aryl and heteroaryl of Ar are each independently optionally substituted with one or more substituents selected from halogen, hydroxyl, $C_1$-$C_{10}$ alkyl, $C_1$-$C_{10}$ alkoxy, $C_3$-$C_{20}$ cycloalkyl, and $C_6$-$C_{20}$ aryl, and the heteroaryl of Ar includes one or more heteroatoms selected from N, O, and S, the method including (1) reacting a compound represented by Formula 2:

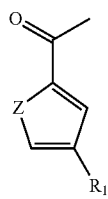
(2)

wherein Z and $R_1$ are as defined in Formula 1, with a compound represented by Formula 3:

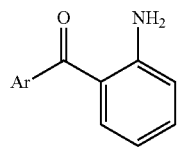
(3)

wherein Ar is as defined in Formula 1, to form a main ligand compound including a quinoline derivative and a thiophene derivative, represented by Formula 4:

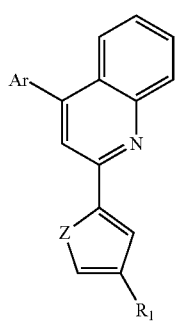
(4)

wherein Ar, Z, and $R_1$ are as defined in Formula 1, (2) reacting the main ligand compound with an iridium halide hydrate ($IrX_3 \cdot 3H_2O$) to form a halide-bridged dimer, and (3) mixing and reacting the halide-bridged dimer with a picolinic acid derivative represented by Formula 5:

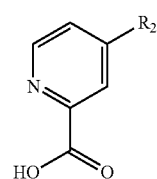
(5)

wherein $R_2$ is as defined in Formula 1.

Preferably, the iridium (III) complex is a red phosphorescent compound and has a structure in which a quinoline-thiophene derivative as a main ligand is introduced and a picolinic acid derivative substituted with a halogen, an oxadiazole derivative having electron transport properties or an mCP derivative having hole transporting properties is introduced as an ancillary ligand at the para-position relative to the nitrogen atom of picolinic acid, which has been described above.

According to one embodiment of the present invention, the mechanism of synthesis of the iridium (III) complex may be depicted as follows:

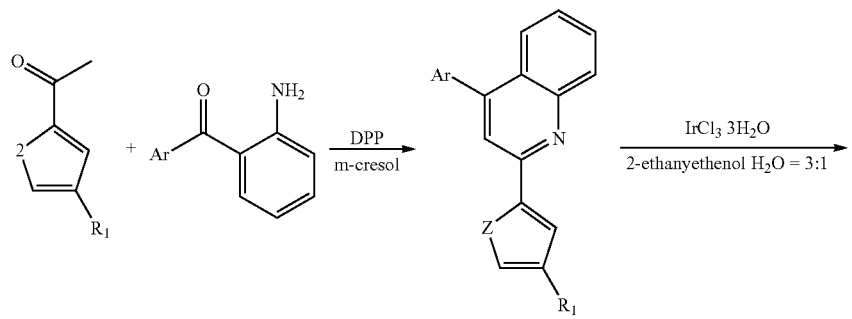

-continued

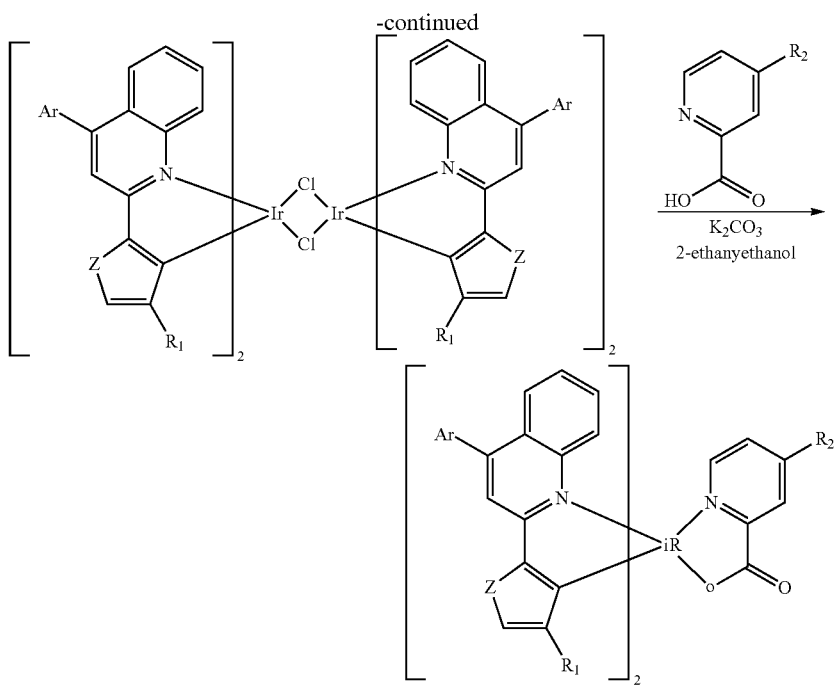

The iridium (III) complex of the present invention can emit pure red light and can be used as a dopant in a light emitting layer to fabricate a red organic electrophosphorescence device by solution processing.

In another aspect, the present invention provides an organic electroluminescence device including a light emitting layer including the iridium (III) complex represented by Formula 1.

More specifically, the organic electroluminescence device includes a first electrode and a second electrode opposite the first electrode wherein the light emitting layer is interposed between the first and second electrodes.

The organic electroluminescence device of the present invention may further include a hole injection layer and a hole transporting layer between the first electrode and the light emitting layer and an electron injection layer and an electron transporting layer between the light emitting layer and the second electrode.

The iridium (III) complex of the present invention may be included as a dopant in the light emitting layer. The iridium (III) complex may be present in an amount of 3 to 20% by weight, based on the total weight of the light emitting layer. Outside the range defined above, the dopant may aggregate or be diluted in the light emitting layer. This aggregation and dilution considerably reduces the efficiency of the organic electroluminescence device. Further, phase separation may occur in the light emitting layer. This phase separation deteriorates the characteristics of the thin film, resulting in poor characteristics, such as low luminance efficiency.

A discussion will be given of a method for fabricating the organic electroluminescence device of the present invention.

FIG. 1 is a cross-sectional view schematically illustrating an organic electroluminescence device 1000 having a monolayer structure in which the iridium complex can be applied in accordance with one embodiment of the present invention. The organic electroluminescence device 1000 has a structure in which a first electrode 1110, a light emitting layer 1140, and a second electrode 1170 are sequentially laminated on a substrate 1100. The substrate 1100 may be made of any suitable material, such as glass or plastic.

Specific examples of materials for the first electrode 1110 include mixed metal oxides, such as indium-tin oxide (ITO), fluorine doped tin oxide (FTO), $ZnO-Ga_2O_3$, $ZnO-Al_2O_3$, and $SnO_2-Sb_2O_3$, and conducting polymers, such as polyaniline and polythiophene. According to a preferred embodiment, the first electrode is made of ITO.

The second electrode 1170 is made of a material effective in injecting electrons as negatively charged carriers. The material for the second electrode 1170 may be: gold, aluminum, copper, silver or an alloy thereof; or an alloy of aluminum, indium, calcium, barium or magnesium, such as a calcium/aluminum, magnesium/silver or aluminum/lithium alloy. The material for the second electrode 1170 may be optionally selected from rare earth metals, lanthanide metals, and actinide metals. Preferably, the second electrode is made of aluminum or an aluminum/calcium alloy.

Phosphorescent hosts usable in the context of the present invention include aryl amine-based, carbazole-based, and spiro-based hosts. Specific examples of such phosphorescent hosts include 4,4-N,N-dicarbazole-biphenyl (CBP), N,N-dicarbazoyl-3,5-benzene (mCP), tris(4-carbazol-9-ylphenyl) amine (TCTA), poly(vinylcarbazole (PVK), polyfluorene, 4,4'-bis[9-(3,6-biphenylcarbazolyl)]-1-1,1'-biphenyl-4,4'-bis[9-(3,6-biphenylcarbazolyl)]-1-1,1'-biphenyl, 9,10-bis(spirobifluorenyl)anthracene, and tetrafluorene. TCTA, CBP, and mCP are preferably used.

The light emitting layer 1140 is laminated on the first electrode 1110 and has a thickness of about 5 to about 200 μm, preferably 50 to 100 μm. The iridium (III) complex of the present invention is used as a dopant and may be included in an amount of 3 to 20% by weight, more specifically 5 to 20% by weight, based on the weight of the light emitting layer 1140.

The iridium complex of the present invention can also be applied to an organic electroluminescence device in the form of a multilayer which includes separate layers for electron/ hole transport between a light emitting layer and electrodes. FIG. 2 is a cross-sectional view schematically illustrating an organic electroluminescence device having a multilayer structure in which the iridium complex of the present invention can be applied. As illustrated in the figure, the organic electroluminescence device 2000 has a structure in which a first electrode 2110, a hole injection layer (HIL) 2120, a hole transporting layer (HTL) 2130, a light emitting layer 2140, an electron transporting layer (ETL) 2150, an electron injection layer (EIL) 2160, and a second electrode 2170 are sequentially laminated on a substrate 2100.

In the organic electroluminescence device 2000 having a multilayer structure, the hole injection layer 2120 is interposed between the first electrode 2110 and the light emitting layer 2140 to improve the interfacial properties between ITO for the first electrode 2100 and an organic material for the hole transporting layer 2130. Another function of the hole injection layer is to make the rough surface of ITO smooth. Particularly, the hole injection layer 2120 functions to moderate the difference between the work function level of ITO for the first electrode 2110 and the HOMO level of the hole transporting layer 2130. Thus, the hole injection layer 2120 has an intermediate value between the work function level of ITO and the HOMO level of the hole transporting layer 2130. Particularly, the material for the hole injection layer 2120 is selected from suitable conducting materials. Examples of materials for the hole injection layer 2120 in the context of the present invention include aromatic amines, such as copper phthalocyanine (CuPc), N,N'-dinaphthyl-N,N'-phenyl-(1,1'-biphenyl)-4,4'-diamine (NPD), 4,4',4"-tris[methylphenyl(phenyl)amino]triphenylamine (m-MTDATA), 4,4',4"-tris[1-naphthyl(phenyl)amino]triphenylamine (1-TNATA), 4,4',4"-tris[2-naphthyl(phenyl) amino]triphenylamine (2-TNATA), and 1,3,5-tris[N-(4-diphenylaminophenyl)phenylamino]benzene (p-DPA-TDAB), and conducting polythiophene derivatives, such as poly(3,4-ethylenedioxythiophene)-poly(styrenesulfonate) (PEDOT). In the Examples section that follows, PEDOT was used as a material for the hole injection layer 2120. The hole injection layer 2120 may be coated to a thickness of 20 to 200 μm on the first electrode 2110.

The hole transporting layer 2130 is formed on the hole injection layer 2120 to stably supply holes entering through the hole injection layer 2120 to the light emitting layer 2140. For smooth hole transport, a material for the hole transporting layer 2130 is selected such that the HOMO level of the hole transporting layer 2130 is higher than that of the light emitting layer 2140. Examples of materials usable for the hole transporting layer 2130 in the context of the present invention include: low molecular weight hole transporting materials, such as N,N'-bis(3-methylphenyl)-N,N'-diphenyl-[1,1'-diphenyl]-4,4'-diamine (TPD), N,N'-bis(1-naphthyl)-N,N'-biphenyl-[1,1'-biphenyl]-4,4'-diamine (TPB), N,N'-di (naphthalen-1-yl)-N,N'-diphenyl-benzidine (NPB), triphenylamine (TPA), bis[4-(N,N-diethylamino)-2-methylphenyl](4-methylphenyl)methane (MPMP), N,N,N',N'-tetrakis(4-methylphenyl)-(1,1'-biphenyl)-4,4-diamine (TTB), and N,N'-bis(4-methylphenyl)-N,N'-bis(4-ethylphenyl)-[1, 1'-(3,3'-dimethyl)biphenyl]-4,4'-diamine (ETPD); and high molecular weight hole transporting materials, such as polyvinylcarbazole, polyaniline, and (phenylmethyl)polysilane. The hole transporting layer 2130 can be deposited to a thickness of about 10 to about 100 μm on the hole injection layer 2120.

According to the present invention, the electron injection layer 2160 and the electron transporting layer 2150 are formed between the light emitting layer 2140 and the second electrode 2170 at positions corresponding to the hole injection layer 2120 and the hole transporting layer 2130, respectively. The electron injection layer 2160 is formed to induce smooth injection of electrons. Unlike the other charge transfer layers, the electron injection layer 2160 is formed using an ionic alkali metal or alkaline earth metal compound, such as LiF, $BaF_2$ or CsF. The electron injection layer 2160 is formed such that doping of the electron transporting layer 2150 with the metal cations can be induced.

The electron transporting layer 2150 is usually composed of a material including an electron withdrawing chemical component. The electron transporting layer 2150 is required to have high electron mobility and stably supplies electrons to the light emitting layer 2140 through smooth electron transport. Suitable materials for the electron transporting layer include $Alq_3$ and oxadizoles. Specific examples of such materials include tris(8-hydroxyquinolinato)aluminum ($Alq_3$), 2,9-dimethyl-4,7-diphenyl-1,10-phenanthroline (DDPA), azole compounds, such as 2-(4-biphenyl)-5-(4-tert-butyl)-1,3,4-oxadiazole (PBD) and 3-(4-biphenyl)-4-phenyl-5-(4-tert-butyl)-1,2,4-triazole (TAZ), phenyl quinoxaline; 3,3'-[5'-[3-(3-pyridinyl)phenyl][1,1':3',1"-terphenyl]-3,3"-diyl]bispyridine (TmPyPB), and 1,3,5-tri(1-phenyl-1H-benzo[d]imidazol-2-yl)phenyl (TPBi). In the Examples section that follows, TmPyPB and TPBi were used for the electron transporting layer 2150. The electron transporting layer 2150 can be laminated to a thickness of 5 to 150 μm on the light emitting layer 2140.

The novel iridium (III) complex, the method for preparing the iridium complex, and the luminescent properties of the device according to the present invention will be explained with reference to the following examples. However, these examples are provided to assist in understanding the invention and are not intended to limit the scope of the invention.

<Preparative Example 1> Preparation of Chloride-Bridged Dimer

The mechanism of synthesis of a chloride-bridged dimer is depicted as follows:

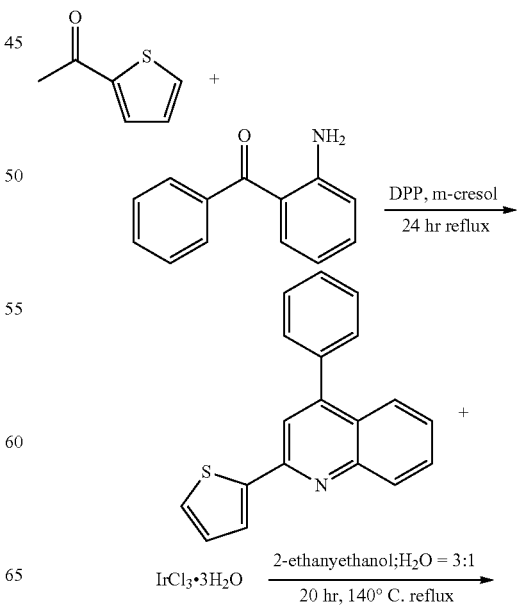

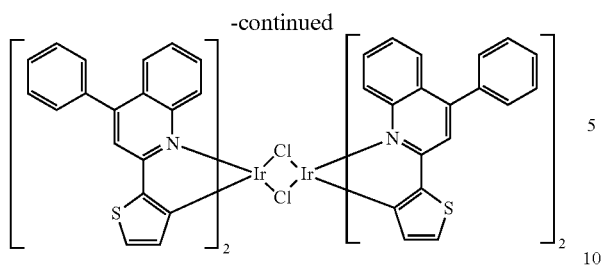

Preparation of 4-phenyl-2-(thiophen-2-yl)quinoline

First, 1.43 g (11.3 mmol) of 1-(thiophene-2-yl)ethanone, 2.46 g (12.5 mmol) of 2-aminobenzophenone, 3.41 g (13.6 mmol) of diphenyl phosphate, and 8.0 mL of m-cresol were placed in a three-neck flask under a nitrogen atmosphere. After stirring at room temperature for 20 min, the mixture was heated to reflux at a temperature of 140° C. for 12 h. Then, the three-neck flask was cooled to room temperature. 60 mL of methylene chloride and 30 mL of a 10% aqueous solution of sodium hydroxide (NaOH) were added to the flask. The organic layer was separated, washed several times with distilled water, dried over magnesium sulfate, and purified by column chromatography using hexane and ethyl acetate, affording 2.5 g (yield 77%) of 4-phenyl-2-(thiophen-2-yl)quinoline. The compound was characterized by $^1$H NMR and $^{13}$C NMR. The results are as follows $^1$H NMR (CDCl$_3$): (ppm) 7.41-7.47 (m, 2H), 7.08-7.19 (m, 3H), 6.83-6.95 (m, 2H), 3.89-3.84 (t, J=7.8 Hz, 2H), 2.58 (s, 3H), 1.82 (m, 2H), 1.25 (m, 4H), 0.98 (t, J=6.6 Hz, 3H);

$^{13}$C NMR (CDCl$_3$): (ppm) 199.8, 144.9, 144.8, 136.1, 132.1, 132.0, 128.2, 122.7, 119.7, 118.9, 47.4, 31.5, 29.3, 27.5, 27.0, 22.7, 14.1

Preparation of the Chloride-Bridged Dimer 5.0 g (17.40 mmol) of 4-phenyl-2-(thiophen-2-yl)quinoline and 2.08 g (6.96 mmol) of iridium chloride hydrate (IrCl$_3$.3H$_2$O) were dissolved in 80 mL of a mixture of 2-ethoxyethanol and distilled water (3:1, v/v). The solution was stirred at a temperature of 140° C. for 24 h. Subsequently, the reaction solution was cooled to room temperature to obtain a yellow solid. The solid was filtered and sufficiently washed with a solution of water and ethanol (3:1, v/v), affording 3.36 g (yield 60%) of the chloride-bridged dimer.

Example 1

Synthesis of Iridium (III) Complex (Th-PQ)$_2$Ir(4-pic-Cl) Having 4-phenyl-2-(thiophen-2-yl)quinoline as Main Ligand and 4-chloropicolinic acid as Ancillary Ligand The mechanism of synthesis of (Th-PQ)$_2$Ir(4-pic-Cl) as an iridium (III) complex is depicted as follows:

20 mL of 2-ethoxyethanol was added to a mixture of 2.3 g (1.44 mmol) of the chloride-bridged dimer prepared in Preparative Example 1, 0.68 g (4.31 mmol) of 4-chloropicolinic acid, and 1.99 g (14.4 mmol) of K$_2$CO$_3$. The resulting mixture was heated to reflux at a temperature of 25° C. for 8 h. Then, the reaction solution was cooled to room temperature to obtain a yellow solid. The solid was filtered and sufficiently washed with a solution of water and ethanol (3:1, v/v), affording 0.84 g (yield 63%) of the iridium complex in which 4-chloropicolinic acid was introduced as an ancillary ligand.

The iridium complex was herein abbreviated as "(Th-PQ)$_2$Ir(4-pic-Cl)". The iridium complex was characterized by NMR. The results are as follows.

$^1$H NMR (300 MHz, CDCl$_3$): (ppm) 8.73-8.70 (d, 1H), 7.96 (s, 1H), 7.85-7.83 (d, 1H), 7.75-7.72 (d, 2H), 7.67-7.63 (m, 3H), 7.61-7.55 (m, 10H), 7.39-7.33 (m, 3H), 7.22-7.15 (m, 3H), 6.96-6.95 (m, 1H), 6.66-6.64 (m, 1H), 6.19-6.17 (m, 1H);

$^{13}$C NMR (300 MHz, CDCl$_3$): (ppm) 171.8, 166.6, 165.2, 154.38, 152.91, 152.82, 151.57, 149.80, 148.96, 147.64, 146.51, 141.52, 139.29, 137.40, 137.36, 134.79, 133.5, 132.20, 130.99, 130.09, 130.01, 129.87, 129.27, 129.13, 128.98, 128.34, 128.27, 126.52, 126.36, 125.88, 125.68, 124.94, 124.79, 117.98, 116.9;

Calcd. for $C_{44}H_{27}ClIrN_3O_2S_2$: C, 57.35; H, 2.95; N, 4.56. Found: C, 57.24; H, 2.82; N, 4.52;

HRESI-MS [M+H]$^+$: m/z found 921.4926, calcd. for 921.49.

Example 2

Synthesis of Iridium Complex (Th-PQ)₂Ir(4-pic-OXD) Having 4-phenyl-2-(thiophen-2-yl)quinoline as Main Ligand and 4-oxadiazolepicolinic acid as Ancillary Ligand The mechanism of synthesis of (Th-PQ)₂Ir(4-pic-OXD) as an iridium (III) complex is depicted as follows:

The iridium complex was herein abbreviated as "(Th-PQ)₂Ir(4-pic-OXD)". The iridium complex was characterized by NMR. The results are as follows.

$^1$H NMR (300 MHz, CDCl$_3$): (ppm) 8.80-8.77 (d, 1H), 8.17-8.15 (m, 4H), 7.87-7.85 (d, 1H), 7.81-7.77 (m, 3H), 7.71 (s, 1H), 7.65-7.57 (m, 16H), 7.41-7.36 (m, 3H), 7.19-7.17 (m, 3H), 7.07-7.02 (m, 2H), 6.70-6.69 (d, 1H), 6.21-6.19 (d, 1H);

$^{13}$C NMR (300 MHz, CDCl$_3$): (ppm) 171.81, 166.86, 165.55, 155.96, 153.57, 151.40, 150.04, 149.05, 139.25, 137.49, 133.62, 132.11, 130.94, 129.88, 129.55, 129.36, 129.03, 128.98, 127.24, 126.63, 126.41, 125.76, 124.93, 124.02, 122.12, 121.69, 115.24;

IR (NaCl cell, cm$^{-1}$): 3057, 2355, 1652, 1596, 1539, 1495, 1452, 1425, 1325, 1290, 1242, 1203, 885, 846, 767, 732, 702, 584;

Calcd. for $C_{58}H_{36}IrN_5O_4S_2$: C, 62.02; H, 3.23; N, 6.23. Found: C, 62.01; H, 3.21; N, 6.20;

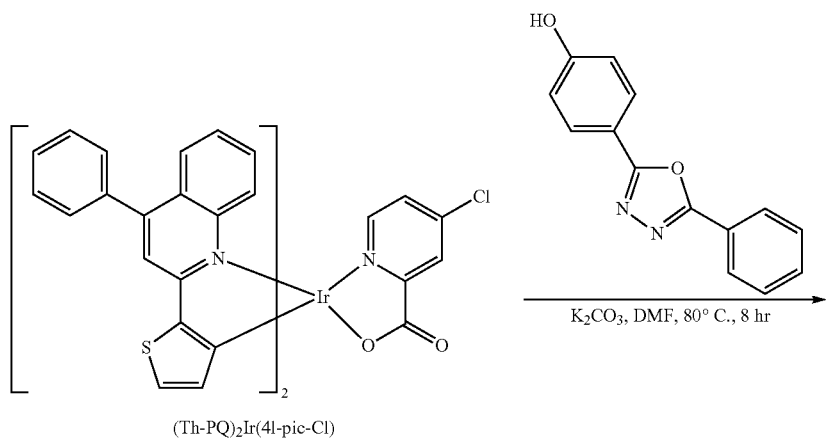

(Th-PQ)₂Ir(4l-pic-Cl)

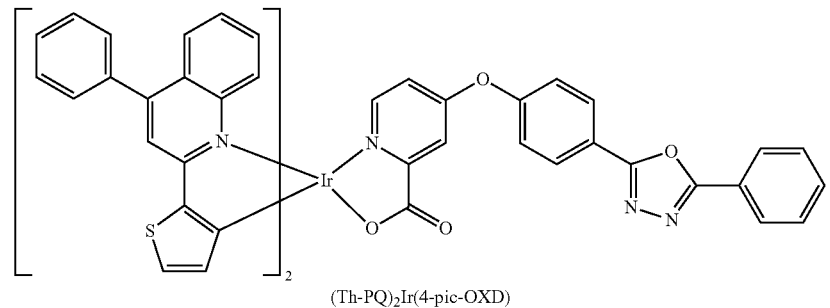

(Th-PQ)₂Ir(4-pic-OXD)

The iridium complex (Th-PQ)₂Ir(4-pic-Cl) synthesized in Example 1 (1 g, 0.57 mmol), 4-(5-phenyl-1,3,4-oxadiazol-2-yl)phenol (1 g, 0.57 mmol), and K₂CO₃ (0.60 g, 5.7 mmol) were dissolved in DMF (10 mL). The solution was heated to reflux at 80° C. under a nitrogen atmosphere for 12 h. After completion of the reaction, the reaction mixture was cooled, added to water, extracted with methylene chloride, dried over anhydrous MgSO₄, and purified by column chromatography using ethyl acetate, methylene chloride, and hexane (3:5:5, v/v/v), affording the iridium complex (0.36 g, yield: 59%).

HRESI-MS [M+H]$^+$: m/z found 1123.2761, calcd. for 1123.27.

Example 3

Synthesis of Iridium (III) Complex Having 4-phenyl-2-(thiophen-2-yl)quinoline as Main Ligand and Picolinic Acid Derivative Substituted with (3,5-di(9H-carbazol-9-yl)phenyl)methanol as Ancillary Ligand The mechanism of synthesis of (Th-PQ)₂Ir(4-pic-mCP) as an iridium (III) complex is depicted as follows:

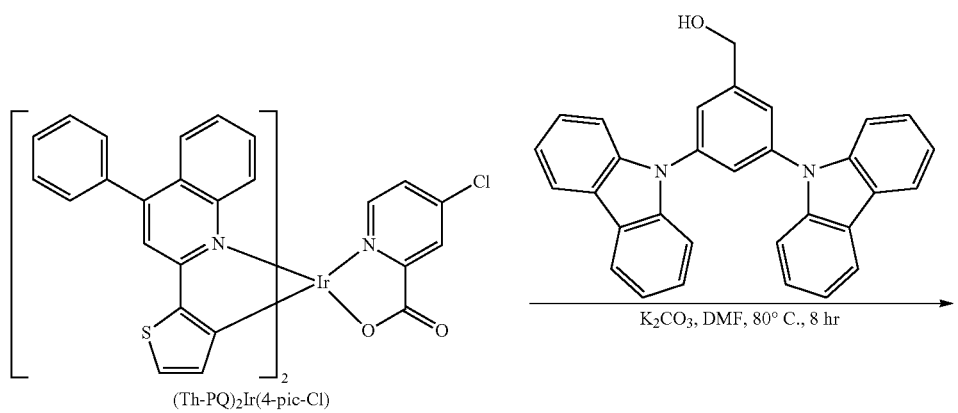

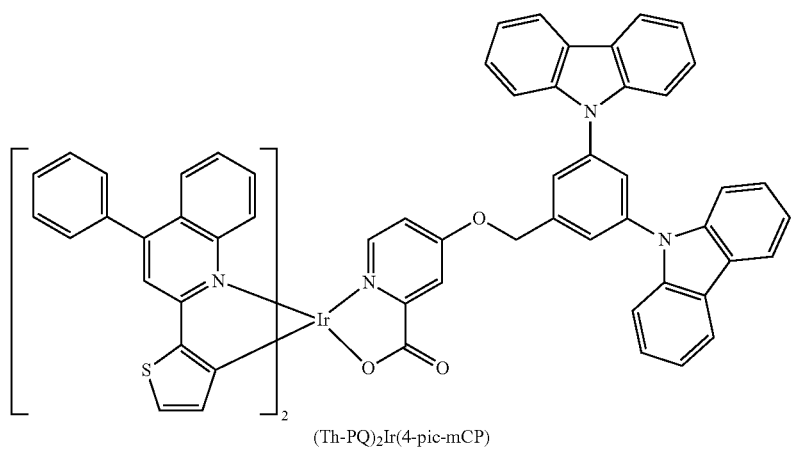

1.0 g (1.09 mmol) of the iridium complex (Th-PQ)₂Ir(4-pic-Cl) obtained in Example 1, 0.52 g (1.20 mmol) of (3,5-di(9H-carbazol-9-yl)phenyl)methanol, and 452 mg (3.27 mmol) of K₂CO₃ were dissolved in 20 mL of DMF in a three-neck flask. The solution was heated to reflux at a temperature of 80° C. under a nitrogen atmosphere for 8 h. After completion of the reaction was confirmed, the reaction mixture was cooled, added to 100 mL of distilled water, extracted three times with 50 mL of methylene chloride, dried over anhydrous MgSO₄, and purified by column chromatography using ethyl acetate and hexane (1:4, v/v), affording 0.59 g (yield 44%) of the iridium (III) complex in which a picolinic acid derivative substituted with (3,5-di (9H-carbazol-9-yl)phenyl)methanol was introduced as an ancillary ligand.

The iridium complex was herein abbreviated as "(Th-PQ)₂Ir(4-pic-mCP)". The iridium complex was characterized by NMR. The results are as follows.

¹H NMR (300 MHz, CDCl₃): (ppm) 8.80-8.77 (d, 1H), 8.17-8.15 (m, 4H), 7.88 (s, 1H), 7.81-7.74 (m, 2H), 7.81-7.74 (m, 5H), 7.68-7.66 (d, 1H), 7.74-7.68 (m, 10H), 7.53 (s, 2H), 7.51 (s, 2H), 7.48-7.40 (m, 4H), 7.38-7.31 (d, 5H), 7.29 (s, 2H), 7.28 (s, 1H), 7.21-7.19 (m, 1H), 7.08-7.06 (m, 2H), 6.92-6.90 (d, 1H), 6.70-6.68 (d, 1H), 6.22-6.20 (d, 1H), 5.28 (s, 2H);

Calcd. for C₇₅H₄₈IrN₃O₃S₂: C, 68.06; H, 3.66; N, 5.29. Found: C, 68.04; H, 3.65; N, 5.25;

HRESI-MS [M+H]⁺: m/z found 1323.2873, calcd. for 1323.56.

Example 4

Synthesis of (9-4(4-(9H-carbazol-9-yl)biphenyl-4-yl)-9H-carbazol-3-yl)methanol (CBP) as Substitutable Derivative The mechanism of synthesis of the substitutable derivative is depicted as follows:

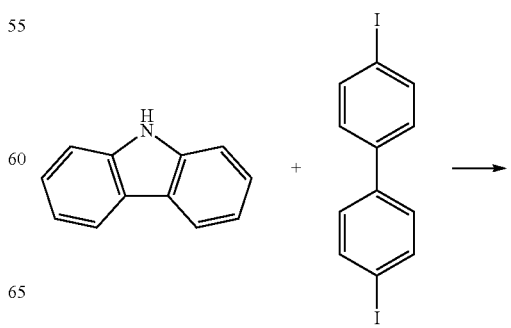

27
-continued

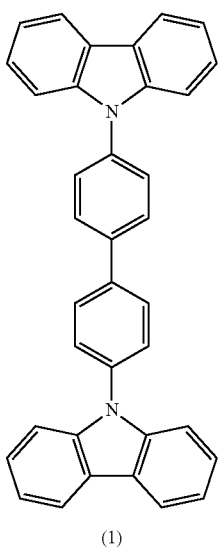
(1)

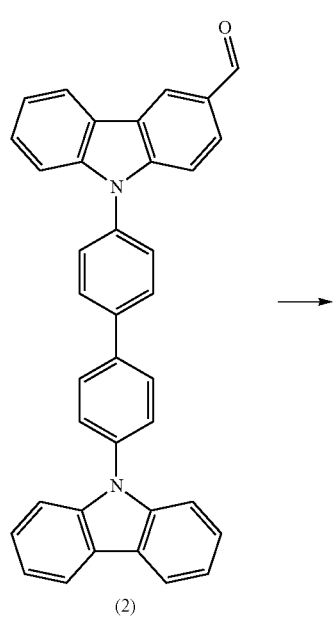
(2)

28
-continued

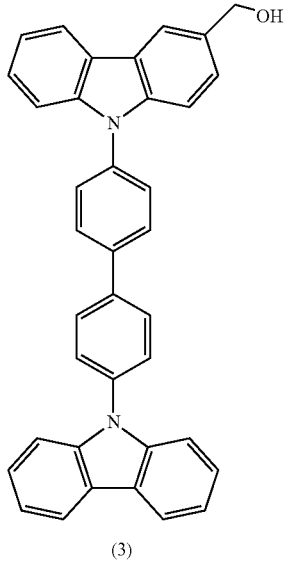
(3)

Synthesis of 4,4-di(9H-carbazol-9-yl)biphenyl (1)

9H-carbazole (350 mg, 2.1 mmol), 4,4-diiodobiphenyl (406 mg, 1.0 mmol), Cu (powder, 63 mg, 1.0 mmol), 18-crown-6 (40 mg, 0.15 mmol), and $K_2CO_3$ (276 mg, 2.0 mmol) were dissolved in o-dichlorobenzene (30 mL) in a three-neck flask (50 mL). The solution was heated to reflux at 180° C. under a nitrogen atmosphere for 16 h. After completion of the reaction was confirmed, the reaction mixture was cooled, added to distilled water (100 mL), extracted three times with chloroform (50 mL), dried over anhydrous $MgSO_4$, and purified by column chromatography using ethyl acetate and hexane (1:4, v/v), affording 4,4-di(9H-carbazol-9-yl)biphenyl (310 mg, yield 62%).

Synthesis of 9-(4-(9H-carbazol-9-yl)biphenyl-4-yl)-9H-carbazol-3-carbaldehyde (2)

A solution of 4,4-di(9H-carbazol-9-yl)biphenyl (300 mg, 0.6 mmol) in chlorobenzene (30 mL) was placed in a three-neck flask and DMF (1.2 mL, 13 mmol) was added thereto. To the mixture was slowly added $POCl_3$ (1.3 mL, 13 mmol) at room temperature under a nitrogen atmosphere. The resulting mixture was heated to reflux at 95° C. for 9 h. After completion of the reaction was confirmed, the reaction mixture was cooled and toxicity was removed therefrom in crushed ice. The nontoxic reaction mixture was extracted three times with chloroform (50 mL), dried over anhydrous $MgSO_4$, and purified by column chromatography using methylene chloride, affording 9-(4-(9H-carbazol-9-yl)biphenyl-4-yl)-9H-carbazol-3-carbaldehyde (105 mg, yield 32%).

Synthesis of (9-4(4-(9H-carbazol-9-yl)biphenyl-4-yl)-9H-carbazol-3-yl)methanol (3)

9-(4-(9H-carbazol-9-yl)biphenyl-4-yl)-9H-carbazol-3-carbaldehyde (100 mg, 0.2 mmol) was dissolved in THF (15 mL) and ethanol (10 mL) in a three-neck flask, and then $NaBH_4$ was added thereto. The mixture was allowed to react at room temperature for 24 h. After completion of the reaction was confirmed, distilled water was slowly added to the reaction mixture. The organic solvent was removed using a rotary evaporator. To the residue were added a 0.1 M aqueous NaOH solution (50 mL) and chloroform (50 mL). Suction filtration gave (9-4(4-(9H-carbazol-9-yl)biphenyl-4-yl)-9H-carbazol-3-yl)methanol (95 mg, 95%) as a white solid.

Comparative Example 1

Synthesis of Iridium (III) Complex (Th-PQ)$_2$Ir(pic) having 4-phenyl-2-(thiophen-2-yl)quinoline as Main Ligand and Picolinic Acid as Ancillary Ligand

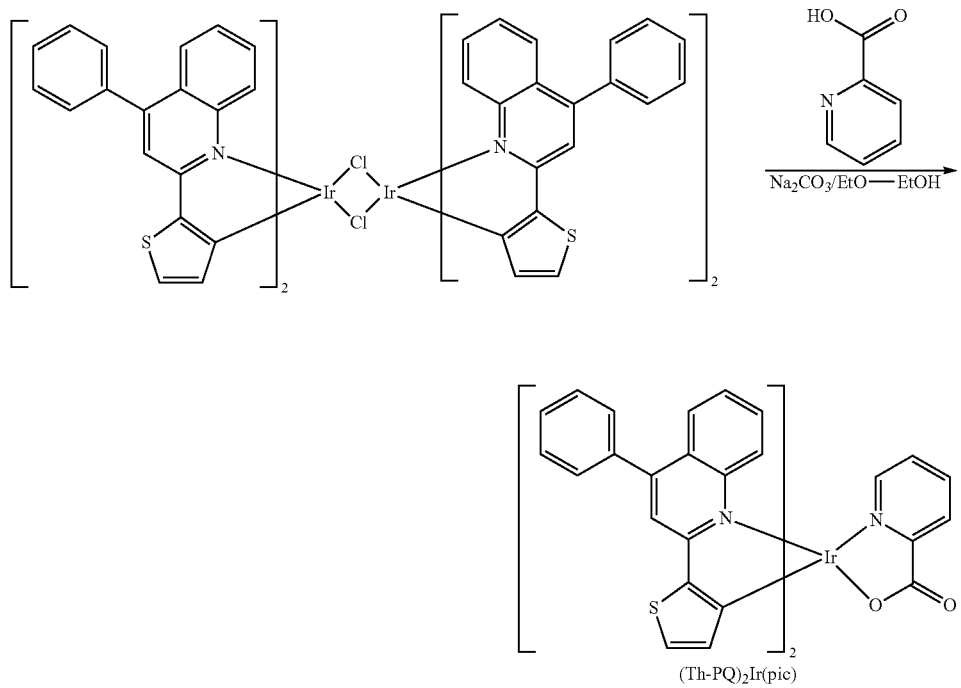

(Th-PQ)$_2$Ir(pic)

1.5 mL of 2-ethoxyethanol was added to a mixture of 49.4 mg (0.048 mmol) of the chloride-bridged dimer obtained in Preparative Example 1 and 15 mg (0.12 mmol) of picolinic acid. The resulting mixture was heated to reflux at a temperature of 25° C. for 20 h. Then, the reaction solution was cooled to room temperature to obtain a solid. The solid was filtered and sufficiently washed with water-ethanol (3:1), affording 20.5 mg (yield 71%) of the iridium (III) complex in which picolinic acid was introduced as an ancillary ligand. The iridium complex was herein abbreviated as "(Th-PQ)$_2$Ir(pic)". The iridium complex was characterized by NMR. The results are as follows.

$^1$H NMR (300 MHz, CDCl$_3$): (ppm) 9.01 (d, J=6 Hz, 2H), 7.59-7.78 (m, 10H), 7.36-7.47 (m, 10H), 6.98-7.20 (m, 8H), 6.83-6.86 (t, J=7.8 Hz, 2H), 5.22 (s, 1H), 3.94-3.89 (t, J=7.2 Hz, 4H), 1.62 (m, 6H), 1.50 (m, 4H), 1.26-1.34 (m, 12H), 0.98 (m, 6H);

$^{13}$C NMR (300 MHz, CDCl$_3$): (ppm) 158.1, 150.5, 148.9, 146.0, 144.9, 145.4, 139.0, 137.9, 135.1, 132.1, 132.0, 129.9, 129.3, 128.9, 128.5, 128.3, 128.2, 127.4, 127.3, 127.0, 119.7, 119.4, 118.8, 118.3, 117.6, 117.0, 116.9, 108.8, 102.4, 59.0, 47.4, 31.5, 27.5, 27.0, 26.6, 25.6, 22.7, 14.1;

Calcd. for C$_{71}$H$_{65}$IrN$_4$O$_2$S$_2$: C, 66.47; H, 4.65; N, 4.70. Found: C, 66.27; H, 4.73; N, 4.72.

Test Example 1

Measurement of Absorption Spectra of the Iridium (III) Complexes

Each of the iridium complexes (Th-PQ)$_2$Ir(4-pic-OXD), (Th-PQ)$_2$Ir(4-pic-mCP), and (Th-PQ)$_2$Ir(pic) as light emitting materials synthesized in Examples 2 and 3 and Comparative Example 1 was dissolved in chloroform. The UV-visible absorption spectrum of the solution was measured using a Shimadzu UV-3100 spectrometer. The results are shown in FIG. 3.

Referring to FIG. 3, the UV absorption peaks show that transitions of the phenyl quinoline-thiophene derivative occurred at wavelengths shorter than 400 nm. For (Th-PQ)$_2$Ir(4-pic-OXD), charge transfer between the singlet and triplet central metal-ligands was observed at a long wavelength of about 492 nm. For (Th-PQ)$_2$Ir(4-pic-mCP), charge transfer between the singlet and triplet central metal-ligands was observed at a long wavelength of about 500 nm.

Test Example 2

Photoluminescence (PL) Measurement of Solutions of the Iridium (III) Complexes

Each of the iridium complexes (Th-PQ)$_2$Ir(4-pic-OXD), (Th-PQ)$_2$Ir(4-pic-mCP), and (Th-PQ)$_2$Ir(pic) as light emitting materials synthesized in Examples 2 and 3 and Comparative Example 1 was dissolved in chloroform. The photoluminescence (PL) spectrum of each solution were measured using Hitachi F-4500. The maximum UV absorption wavelength measured in the iridium-based light emitting material was set as the excitation wavelength for PL measurement. The results are shown in FIG. 4.

Referring to FIG. 4, the photoluminescence (PL) spectra show that the iridium complexes (Th-PQ)$_2$Ir(4-pic-OXD), (Th-PQ)$_2$Ir(4-pic-mCP), and (Th-PQ)$_2$Ir(pic) as light emitting materials emitted red light at around 610 nm despite the different structures of the ancillary ligands.

Test Example 3

Characterization of OLED Devices Including the Iridium (III) Complexes

Each of the iridium complex (Th-PQ)$_2$Ir(4-pic-OXD) of Example 2 and the iridium complex (Th-PQ)$_2$Ir(pic) of Comparative Example 1 was used to fabricate an OLED device having an ITO/PEDOT:PSS/TCTA:TPBi:iridium complex/PmPyPB/LiF/Al structure.

Each of the iridium complex (Th-PQ)$_2$Ir(4-pic-mCP) of Example 3 and the iridium complex (Th-PQ)$_2$Ir(pic) of Comparative Example 1 was used to fabricate an OLED device having an ITO/PEDOT:PSS/TCTA:TPBi:iridium complex/TPBi/LiF/Al structure.

To characterize the OLED devices, EL spectra (Hitachi F-4500 fluorescence spectrophotometer), current density-voltage-luminance characteristics (Keithley 238, CS-1000, LS-100), and external quantum efficiencies as a function of luminance were measured. The results are shown in FIGS. 5 to 7.

Iridium (III) bis(2-(2-benzothienyl)pyridinato-N,C2) (acetylacetonate) ("Ir(btp)$_2$(acac)" disclosed in the prior art document (U.S. Pat. No. 7,250,512) was used to fabricate an OLED device having an ITO/NPD/CBP:Ir(btp)$_2$(acac)/BCP/Alq$_3$/MgAg/Ag structure (Comparative Test Example 1). The external quantum efficiencies of the device as a function of luminance were measured. The results are shown in FIG. 8.

An explanation will be given of the results of the test examples with reference to the figures.

FIG. 5 shows the EL spectra of the iridium complexes (Th-PQ)$_2$Ir(4-pic-OXD), (Th-PQ)$_2$Ir(4-pic-mCP), and (Th-PQ)$_2$Ir(pic) as light emitting materials synthesized in Examples 2 and 3 and Comparative Example 1, respectively. The iridium complexes showed maximum emission peaks between 623 and 625 nm and had color coordinates (0.675, 0.323), indicating high color purities.

Ir(btp)$_2$(acac) of the prior art document (U.S. Pat. No. 7,250,512) showed a maximum emission peak at about 620 nm and an emission peak at 675 nm. In contrast, the inventive iridium complexes showed maximum emission peaks at 625 and 623 nm, indicating further improvements in red luminescent properties and color purity.

FIG. 6 shows the current density-voltage-luminance characteristics of the organic electroluminescence devices including the iridium complexes (Th-PQ)$_2$Ir(4-pic-OXD), (Th-PQ)$_2$Ir(4-pic-mCP), and (Th-PQ)$_2$Ir(pic) as light emitting materials synthesized in Examples 2 and 3 and Comparative Example 1. The iridium complexes (Th-PQ)$_2$Ir(4-pic-OXD), (Th-PQ)$_2$Ir(4-pic-mCP), and (Th-PQ)$_2$Ir(pic) had driving voltages of about 6 V, about 8.72 V, and about 8.53 V, respectively, and maximum luminance values of 1350 cd/m$^2$, 3013 cd/m$^2$, and 2985 cd/m$^2$, respectively.

FIG. 7 shows the luminance efficiencies and power efficiencies of the iridium complexes (Th-PQ)$_2$Ir(4-pic-OXD), (Th-PQ)$_2$Ir(4-pic-mCP), and (Th-PQ)$_2$Ir(pic) as light emitting materials synthesized in Examples 2 and 3 and Comparative Example 1 as a function of current density. The maximum luminance efficiencies of the iridium complexes (Th-PQ)$_2$Ir(4-pic-OXD) (Example 2) and (Th-PQ)$_2$Ir(4-pic-mCP) (Example 3) were 11.19 cd/A % and 9.95 cd/A %, respectively, whereas the maximum luminance efficiency of the iridium complex (Th-PQ)$_2$Ir(pic) (Comparative Example 1) was 6.14 cd/A. These results demonstrate that the introduction of the OXD and mCP derivatives as ancillary ligands at the 4-position of picolinic acid in the iridium (III) complexes having the same structure ensures excellent characteristics in terms of maximum external quantum efficiency, luminance efficiency, and power efficiency.

FIG. 8 shows the external quantum efficiencies of Ir(btp)$_2$(acac) as a function of luminance in the organic electroluminescence device of Comparative Test Example 1. The maximum external quantum efficiency of Ir(btp)$_2$(acac) was found to be 6%.

The introduction of substituents other than hydrogen as ancillary ligands at the 4-position of picolinic acid in the inventive iridium (III) complexes having the same structure led to significant improvements in maximum external quantum efficiency, luminance efficiency, and power efficiency, achieving very high external quantum efficiencies of the inventive iridium (III) complexes.

The invention claimed is:

1. An iridium (III) complex represented by Formula 1:

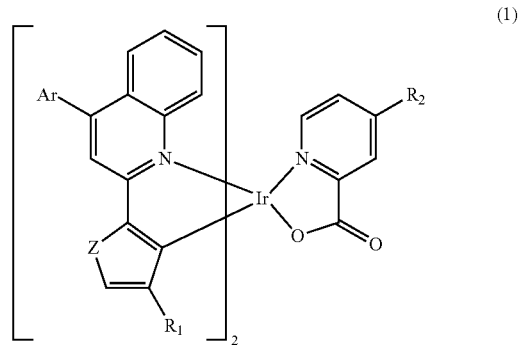

(1)

wherein Ar is C$_6$-C$_{20}$ aryl or C$_3$-C$_{20}$ heteroaryl,

Z is O, S or Se,

R$_1$ is hydrogen, halogen, C$_1$-C$_{20}$ alkyl, C$_1$-C$_{20}$ alkoxy, cyano or nitro, R$_2$ is

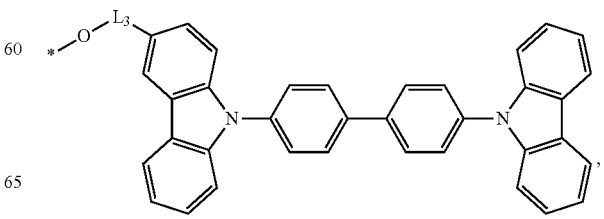

-continued

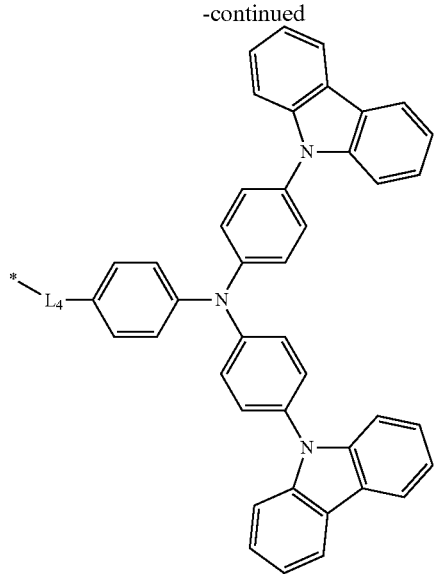

or

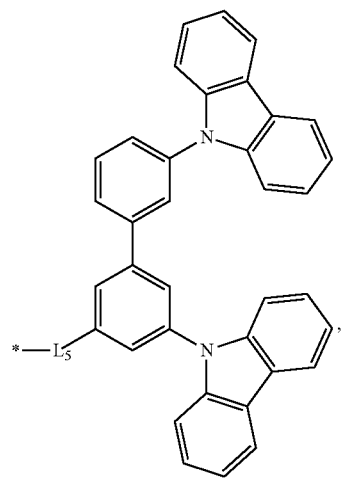

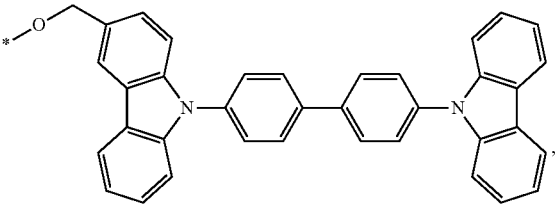

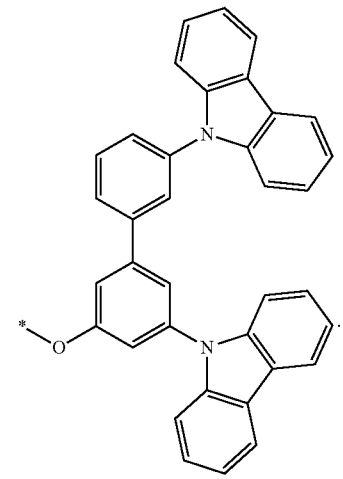 [SMILES: *Oc1cc(-c2cccc(-n3c4ccccc4c4ccccc43)c2)cc(-n2c3ccccc3c3ccccc32)c1]

or $L_3$ is $C_1$-$C_{20}$ alkylene, $L_4$ and $L_5$ are each independently O or $C_1$-$C_{20}$ alkylene-oxy, the aryl and heteroaryl of Ar are each independently optionally substituted with one or more substituents selected from halogen, hydroxy, $C_1$-$C_{10}$ alkyl, $C_1$-$C_{10}$ alkoxy, $C_3$-$C_{20}$ cycloalkyl, or $C_6$-$C_{20}$ aryl, and the heteroaryl of Ar comprises one or more heteroatoms selected from N, O, or S.

2. The iridium (III) complex according to claim 1, wherein Ar is $C_6$-$C_{20}$ aryl, Z is S, and $R_1$ is hydrogen.

3. The iridium (III) complex according to claim 2, wherein $R_2$ is

4. The iridium (III) complex according to claim 1, wherein the iridium (III) complex is selected from:

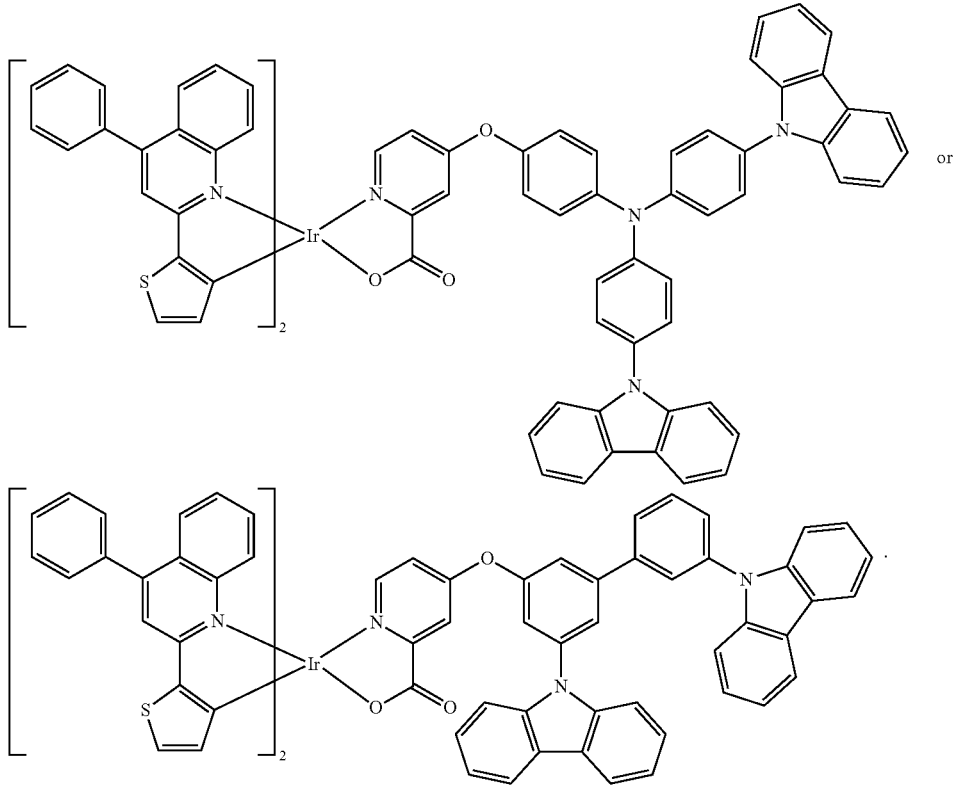

5. An organic electroluminescence device comprising a light emitting layer comprising the iridium (III) complex according to claim 1.

6. The organic electroluminescence device according to claim 5, wherein the organic electroluminescence device comprises a first electrode and a second electrode opposite to each other between which the light emitting layer is interposed.

7. The organic electroluminescence device according to claim 6, further comprising a hole injection layer and a hole transporting layer between the first electrode and the light emitting layer, and an electron injection layer and an electron transporting layer between the light emitting layer and the second electrode.

8. The organic electroluminescence device according to claim 5, wherein the light emitting layer comprises the iridium (III) complex as a dopant.

9. The organic electroluminescence device according to claim 8, wherein the iridium (III) complex is present in an amount of 3 to 20% by weight, based on the total weight of the light emitting layer.

10. An iridium (III) complex represented by Formula 1:

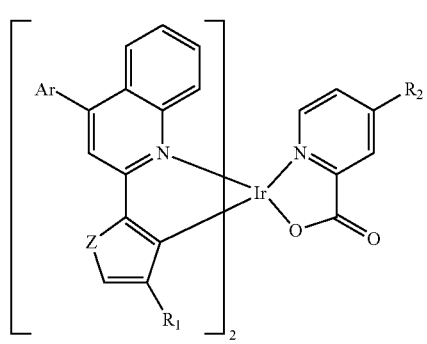

(1)

wherein Ar is $C_6$-$C_{20}$ aryl or $C_3$-$C_{20}$ heteroaryl,

Z is O, S or Se, $R_1$ is hydrogen, halogen, $C_1$-$C_{20}$ alkyl, $C_1$-$C_{20}$ alkoxy, cyano or nitro, R₂ is

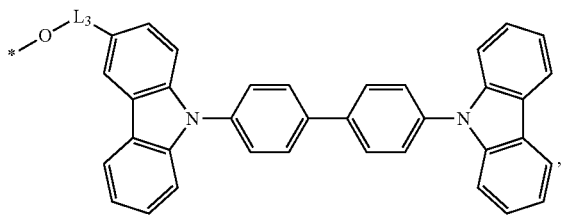

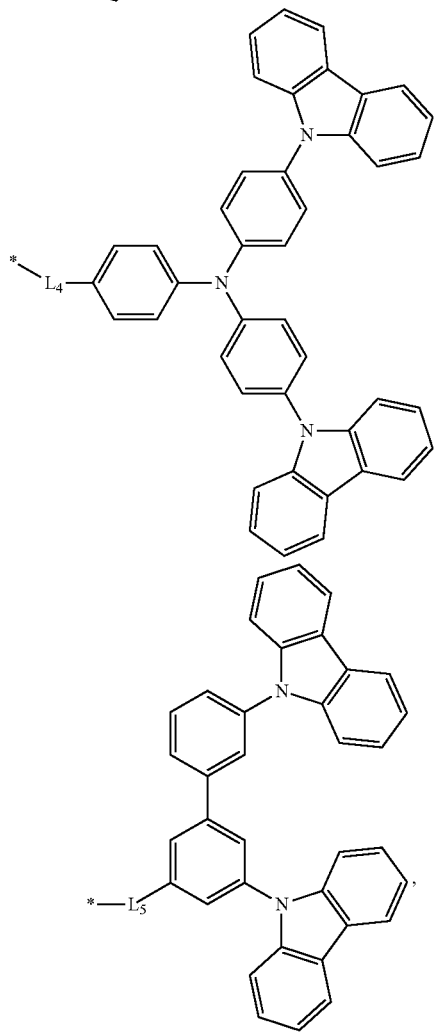

or

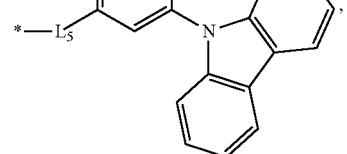

L₁ is C₆-C₂₀ arylene,

Ar₁ is C₆-C₂₀ aryl, the aryl and heteroaryl of Ar are each independently optionally substituted with one or more substituents selected from halogen, hydroxy, C₁-C₁₀ alkyl, C₁-C₁₀ alkoxy, C₃-C₂₀ cycloalkyl, or C₆-C₂₀ aryl, and the heteroaryl of Ar comprises one or more heteroatoms selected from N, O, or S.

11. The iridium (III) complex according to claim 10, wherein Ar is C₆-C₂₀ aryl, Z is S, R₁ is hydrogen, L₁ is C₆-C₂₀ arylene, and Ar₁ is C₆-C₂₀ aryl.

12. The iridium (III) complex according to claim 10, wherein R₂ is

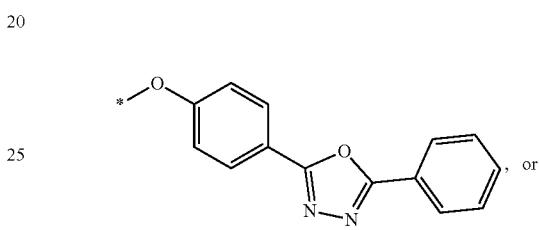

, or

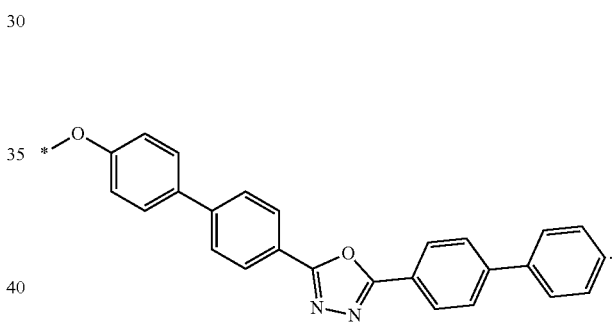

.

13. The iridium (III) complex according to claim 10, wherein the iridium (III) complex is selected from:

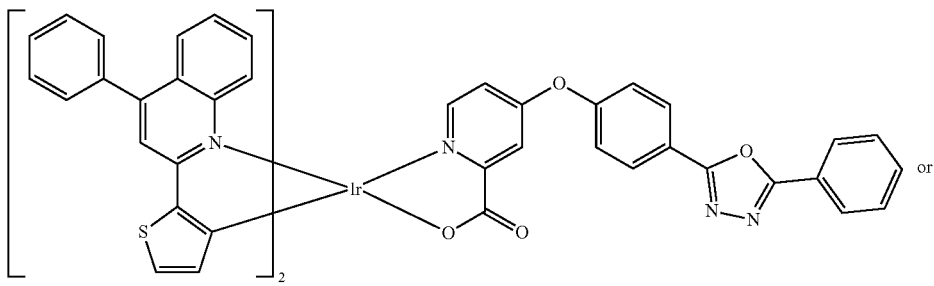

or

-continued

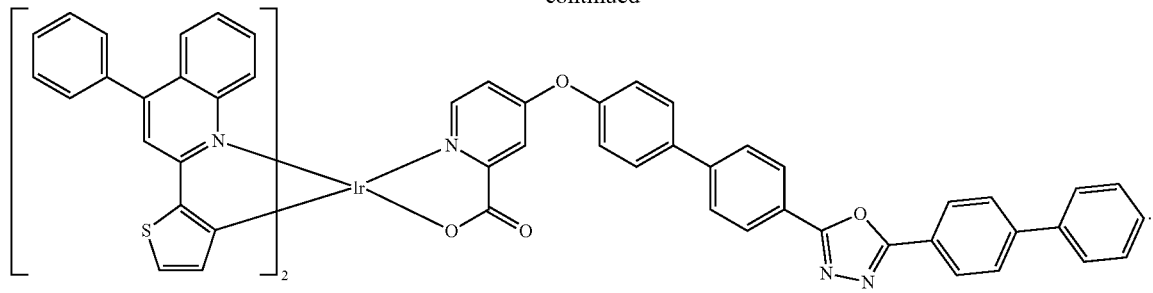

14. An organic electroluminescence device comprising a light emitting layer comprising the iridium (III) complex according to claim 10.

15. The organic electroluminescence device according to claim 14, wherein the organic electroluminescence device comprises a first electrode and a second electrode opposite to each other between which the light emitting layer is interposed.

16. The organic electroluminescence device according to claim 15, further comprising a hole injection layer and a hole transporting layer between the first electrode and the light emitting layer, and an electron injection layer and an electron transporting layer between the light emitting layer and the second electrode.

17. The organic electroluminescence device according to claim 14, wherein the light emitting layer comprises the iridium (III) complex as a dopant.

18. The organic electroluminescence device according to claim 14, wherein the iridium (III) complex is present in an amount of 3 to 20% by weight, based on the total weight of the light emitting layer.

* * * * *